(12) United States Patent
Takeuchi et al.

(10) Patent No.: US 8,729,110 B1
(45) Date of Patent: May 20, 2014

(54) 2-THIO-1,3,4-OXADIAZOLES DERIVATIVES AS SPHINGOSINE-1 PHOSPHATE RECEPTORS MODULATORS

(71) Applicant: Allergan, Inc., Irvine, CA (US)

(72) Inventors: Janet A. Takeuchi, Anaheim, CA (US); Ling Li, Irvine, CA (US); Wha-Bin Im, Irvine, CA (US); Ken Chow, Newport Coast, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/073,970

(22) Filed: Nov. 7, 2013

(65) Prior Publication Data

US 2014/0135291 A1    May 15, 2014

Related U.S. Application Data

(60) Provisional application No. 61/726,197, filed on Nov. 14, 2012.

(51) Int. Cl.
*A61K 31/4245*  (2006.01)
*C07D 271/07*  (2006.01)

(52) U.S. Cl.
CPC .................................. *C07D 271/07* (2013.01)
USPC ......................................... 514/364; 548/132

(58) Field of Classification Search
USPC ........................................ 514/364; 548/132
See application file for complete search history.

(56) References Cited

U.S. PATENT DOCUMENTS 5,670,526 A * 9/1997 Dodd et al. .................. 514/340

FOREIGN PATENT DOCUMENTS

WO    2012-071212 A2    5/2012
WO    2012-074732 A1    6/2012

OTHER PUBLICATIONS

Poveda, Brima et al, Preparation of Thiadiazole Derivatives as Agonists of S1P1 Receptors, Database CA Chemical Abstracts Service, 2011, STN: 2011-434512.
International Search Report for PCT/US2013/069218, Jan. 20, 2014.
Cross, L.C. et al, Rules for the Nomenclature of Organic Chemistry, Section E: Stereochemistry, Pure & Appl. Chem., 1976, 11-30, 45.
Stahl, Heinrich et al, Handbook of Pharmaceutical Salts, Verlag Helvetica Chimica Acta—Zurich, 2002, 329-345.

* cited by examiner

*Primary Examiner* — Rebecca Anderson
*Assistant Examiner* — Karen Cheng
(74) *Attorney, Agent, or Firm* — Doina G. Ene

(57) ABSTRACT

The present invention relates to novel 2-thio-1,3,4-oxadiazoles derivatives, processes for preparing them, pharmaceutical compositions containing them and their use as pharmaceuticals as modulators of sphingosine-1-phosphate receptors.

10 Claims, No Drawings

2-THIO-1,3,4-OXADIAZOLES DERIVATIVES AS SPHINGOSINE-1 PHOSPHATE RECEPTORS MODULATORS

RELATED APPLICATION

This application claims the benefit of U.S. Provisional Patent Application Ser. No. 61/726,197 filed Nov. 14, 2012, the disclosure of which is hereby incorporated in its entirety herein by reference.

FIELD OF THE INVENTION

The present invention relates to 2-thio-1,3,4-oxadiazoles derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect, the invention provides a compound having Formula I or a pharmaceutically acceptable salt thereof or stereoisomeric forms thereof, enantiomers, diastereoisomers, tautomers, zwitterions and pharmaceutically acceptable salts thereof:

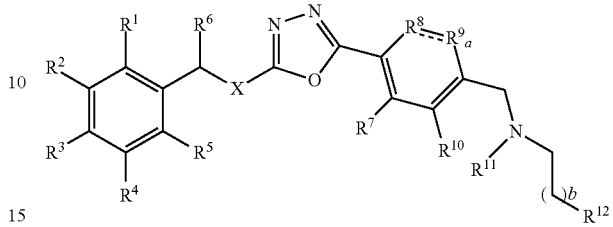

Formula I wherein:

$X$ is $S$, $SO$ or $SO_2$;

$R^1$ is hydrogen, halogen, substituted or unsubstituted $C_{1-8}$ alkyl, $NO_2$, $CN$, $C(O)R^{13}$ or $OR^{14}$;

$R^2$ is hydrogen, halogen, substituted or unsubstituted $C_{1-8}$ alkyl, $NO_2$, $CN$, $C(O)R^{13}$ or $OR^{14}$;

$R^3$ is hydrogen, halogen, substituted or unsubstituted $C_{1-8}$ alkyl, $NO_2$, $CN$, $C(O)R^{13}$ or $OR^{14}$;

$R^4$ is hydrogen, halogen, substituted or unsubstituted $C_{1-8}$ alkyl, $NO_2$, $CN$, $C(O)R^{13}$ or $OR^{14}$;

$R^5$ is hydrogen, halogen, substituted or unsubstituted $C_{1-8}$ alkyl, $NO_2$, $CN$, $C(O)R^{13}$ or $OR^{14}$;

$R^6$ is H, halogen, $OR^{14}$, substituted or unsubstituted $C_{1-8}$ alkyl;

$R^7$ is hydrogen, halogen, substituted or unsubstituted $C_{1-8}$ alkyl, $NO_2$, $CN$, $C(O)R^{13}$ or $OR^{14}$;

$R^8$ is $CH$, $S$, $O$, $N$, $NH$ or $CH_2$;

$R^9$ is $CH$ or $CH_2$;

$R^{10}$ is hydrogen, halogen, substituted or unsubstituted $C_{1-8}$ alkyl, $C(O)R^{13}$ or $OR^{14}$;

$R^{11}$ is H or substituted or unsubstituted $C_{1-8}$ alkyl;

$R^{12}$ is $OPO_3H_2$, carboxylic acid, $PO_3H_2$, —$P(O)MeOH$, —$P(O)(H)OH$ or $OR^{14}$;

a is 0 or 1;

b is 1, 2, 3, 4, 5 or 6;

$R^{13}$ is $OH$ or $C_{1-8}$ alkyl;

$R^{14}$ is H or $C_{1-8}$ alkyl;

when a is 1 then

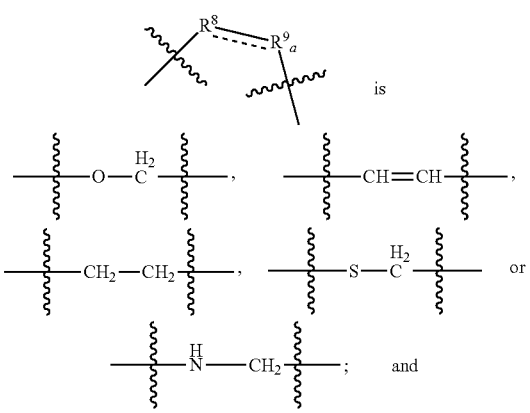

when a is 0 then

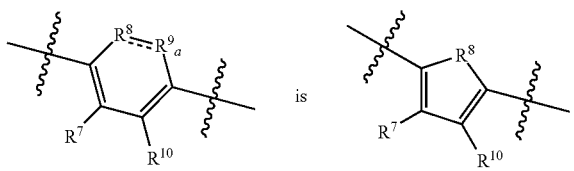

and $R^8$ is S, O, NH or $CH_2$.

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;
$R^7$ is hydrogen, halogen, substituted or unsubstituted $C_{1-8}$ alkyl, $NO_2$, CN, $C(O)R^{13}$ or $OR^{14}$;
$R^8$ is CH;
$R^9$ is CH;
$R^{10}$ is hydrogen, halogen, substituted or unsubstituted $C_{1-8}$ alkyl, $C(O)R^{13}$ or $OR^{14}$;
$R^{11}$ is H or substituted or unsubstituted $C_{1-8}$ alkyl;
$R^{12}$ is $OPO_3H_2$, carboxylic acid, $PO_3H_2$, —P(O)MeOH, —P(O)(H)OH or $OR^{14}$;
a is 1;
b is 1, 2, 3, 4, 5 or 6;
$R^{13}$ is OH or $C_{1-8}$ alkyl;
$R^{14}$ is H or $C_{1-8}$ alkyl; and

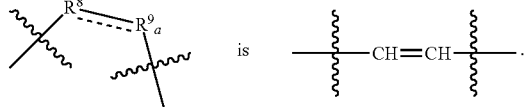

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;
$R^7$ is hydrogen, halogen, substituted or unsubstituted $C_{1-8}$ alkyl, $NO_2$, CN, $C(O)R^{13}$ or $OR^{14}$;
$R^8$ is S or O;

$R^{10}$ is hydrogen, halogen, substituted or unsubstituted $C_{1-8}$ alkyl, $C(O)R^{13}$ or $OR^{14}$;
$R^{11}$ is H or substituted or unsubstituted $C_{1-8}$ alkyl;
$R^{12}$ is $OPO_3H_2$, carboxylic acid, $PO_3H_2$, —P(O)MeOH, —P(O)(H)OH or $OR^{14}$;
a is 0;
b is 1, 2, 3, 4, 5 or 6;
$R^{13}$ is OH or $C_{1-8}$ alkyl; and
$R^{14}$ is H or $C_{1-8}$ alkyl.

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;
$R^7$ is hydrogen, halogen, substituted or unsubstituted $C_{1-8}$ alkyl, $NO_2$, CN, $C(O)R^{13}$ or $OR^{14}$;
$R^8$ is CH;
$R^9$ is CH;
$R^{10}$ is hydrogen, halogen, substituted or unsubstituted $C_{1-8}$ alkyl, $C(O)R^{13}$ or $OR^{14}$;
$R^{11}$ is H or substituted or unsubstituted $C_{1-8}$ alkyl;
$R^{12}$ is carboxylic acid, $PO_3H_2$ or $OR^{14}$;
a is 1;
b is 1, 2, 3, 4, 5 or 6;
$R^{13}$ is OH or $C_{1-8}$ alkyl;
$R^{14}$ is H or $C_{1-8}$ alkyl; and

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;
$R^7$ is hydrogen, halogen, substituted or unsubstituted $C_{1-8}$ alkyl, $NO_2$, CN, $C(O)R^{13}$ or $OR^{14}$;
$R^8$ is CH;
$R^9$ is CH;
$R^{10}$ is hydrogen, halogen, substituted or unsubstituted $C_{1-8}$ alkyl, $C(O)R^{13}$ or $OR^{14}$;

$R^{11}$ is H or substituted or unsubstituted $C_{1-8}$ alkyl;
$R^{12}$ is carboxylic acid;
a is 1;
b is 1, 2, 3, 4, 5 or 6;
$R^{13}$ is OH or $C_{1-8}$ alkyl;
$R^{14}$ is H or $C_{1-8}$ alkyl; and $\begin{array}{c}\text{R}^8\text{\ \ R}^9_a\end{array}$ is $-\text{CH}=\text{CH}-$.

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;
$R^7$ is hydrogen, halogen, substituted or unsubstituted $C_{1-8}$ alkyl, $NO_2$, CN, $C(O)R^{13}$ or $OR^{14}$;
$R^8$ is CH;
$R^9$ is CH;
$R^{10}$ is hydrogen, halogen, substituted or unsubstituted $C_{1-8}$ alkyl, $C(O)R^{13}$ or $OR^{14}$;
$R^{11}$ is H or substituted or unsubstituted $C_{1-8}$ alkyl;
$R^{12}$ is $PO_3H_2$;
a is 1;
b is 1, 2, 3, 4, 5 or 6;
$R^{13}$ is OH or $C_{1-8}$ alkyl;
$R^{14}$ is H or $C_{1-8}$ alkyl; and $\begin{array}{c}\text{R}^8\text{\ \ R}^9_a\end{array}$ is $-\text{CH}=\text{CH}-$.

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;

$R^7$ is hydrogen, halogen, substituted or unsubstituted $C_{1-8}$ alkyl, $NO_2$, CN, $C(O)R^{13}$ or $OR^{14}$;
$R^8$ is CH;
$R^9$ is CH;
$R^{10}$ is hydrogen, halogen, substituted or unsubstituted $C_{1-8}$ alkyl, $C(O)R^{13}$ or $OR^{14}$;
$R^{11}$ is H or substituted or unsubstituted $C_{1-8}$ alkyl;
$R^{12}$ is $OR^{14}$;
a is 1;
b is 1, 2, 3, 4, 5 or 6;
$R^{13}$ is OH or $C_{1-8}$ alkyl;
$R^{14}$ is H; and $\begin{array}{c}\text{R}^8\text{\ \ R}^9_a\end{array}$ is $-\text{CH}=\text{CH}-$.

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;
$R^7$ is hydrogen, halogen, substituted or unsubstituted $C_{1-8}$ alkyl, $NO_2$, CN, $C(O)R^{13}$ or $OR^{14}$;
$R^8$ is O;
$R^{10}$ is hydrogen, halogen, substituted or unsubstituted $C_{1-8}$ alkyl, $C(O)R^{13}$ or $OR^{14}$;
$R^{11}$ is H or substituted or unsubstituted $C_{1-8}$ alkyl;
$R^{12}$ is $OPO_3H_2$, carboxylic acid, $PO_3H_2$, —P(O)MeOH, —P(O)(H)OH or $OR^{14}$;
a is 0;
b is 1, 2, 3, 4, 5 or 6;
$R^{13}$ is OH or $C_{1-8}$ alkyl; and
$R^{14}$ is H or $C_{1-8}$ alkyl.

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;
$R^7$ is hydrogen, halogen, substituted or unsubstituted $C_{1-8}$ alkyl, $NO_2$, CN, $C(O)R^{13}$ or $OR^{14}$;
$R^8$ is S;

$R^{10}$ is hydrogen, halogen, substituted or unsubstituted $C_{1-8}$ alkyl, $C(O)R^{13}$ or $OR^{14}$;
$R^{11}$ is H or substituted or unsubstituted $C_{1-8}$ alkyl;
$R^{12}$ is $OPO_3H_2$, carboxylic acid, $PO_3H_2$, —$P(O)MeOH$, —$P(O)(H)OH$ or $OR^{14}$;
a is 0;
b is 1, 2, 3, 4, 5 or 6;
$R^{13}$ is OH or $C_{1-8}$ alkyl; and
$R^{14}$ is H or $C_{1-8}$ alkyl.

In another aspect, the invention provides a compound having Formula I
wherein:
X is S;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;
$R^7$ is hydrogen, halogen, substituted or unsubstituted $C_{1-8}$ alkyl, $NO_2$, CN, $C(O)R^{13}$ or $OR^{14}$;
$R^8$ is S or O;
$R^{10}$ is hydrogen, halogen, substituted or unsubstituted $C_{1-8}$ alkyl, $C(O)R^{13}$ or $OR^{14}$;
$R^{11}$ is H or substituted or unsubstituted $C_{1-8}$ alkyl;
$R^{12}$ is $PO_3H_2$;
a is 0;
b is 1, 2, 3, 4, 5 or 6;
$R^{13}$ is OH or $C_{1-8}$ alkyl; and
$R^{14}$ is H or $C_{1-8}$ alkyl.

The term "alkyl", as used herein, refers to saturated, monovalent or divalent hydrocarbon moieties having linear or branched moieties or combinations thereof and containing 1 to 8 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by 1 to 3 $C_{1-8}$ alkyl groups or 1 or 2 halogens.

The term "cycloalkenyl", as used herein, refers to a monovalent or divalent group of 3 to 8 carbon atoms, derived from a saturated cycloalkyl having one double bond. Cycloalkenyl groups can be monocyclic or polycyclic. Cycloalkenyl groups can be substituted by 1 to 3 $C_{1-8}$ alkyl groups or 1 or 2 halogens.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by 1 to 2 $C_{1-3}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be saturated or non-saturated. The heterocyclic ring can be interrupted by a C=O; the S heteroatom can be oxidized. Heterocycles can be monocyclic or polycyclic. Heterocyclic ring moieties can be substituted by hydroxyl, 1 to 2 $C_{1-8}$ alkyl or 1 to 2 halogens.

The term "aryl" as used herein, refers to an organic moiety derived from an aromatic hydrocarbon consisting of a ring containing 6 to 10 carbon atoms by removal of one hydrogen, which can be substituted by 1 to 3 halogen atoms or by 1 to 2 $C_{1-8}$ alkyl groups. Usually aryl is phenyl.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$".

The term "sulfate" as used herein, represents a group of formula "—O—$S(O)_2$—O—".

The term "carboxylic acid" as used herein, represents a group of formula "—C(O)ON".

The term "sulfoxide" as used herein, represents a group of formula "—S=O".

The term "phosphonic acid" as used herein, represents a group of formula "—$P(O)(OH)_2$".

The term "phosphoric acid" as used herein, represents a group of formula "—$(O)P(O)(OH)_2$".

The term "sulphonic acid" as used herein, represents a group of formula "—$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:
3-[(4-{5-[(3-Chloro-2-fluorobenzyl)thio]-1,3,4-oxadiazol-2-yl}benzyl)amino]propanoic acid;
2-[(4-{5-[(3-Chloro-2-fluorobenzyl)thio]-1,3,4-oxadiazol-2-yl}benzyl)amino]ethyl dihydrogen phosphate;
2-[(4-{5-[(3-Chloro-2-fluorobenzyl)thio]-1,3,4-oxadiazol-2-yl}benzyl)amino]ethanol;
3-{[3-methyl-4-(5-{[1-(3-nitrophenyl)ethyl]thio}-1,3,4-oxadiazol-2-yl)benzyl]amino}propanoic acid;
(3-{[3-Methyl-4-(5-{[1-(3-nitrophenyl)ethyl]thio}-1,3,4-oxadiazol-2-yl)benzyl]amino}propylphosphonic acid;
(3-{[3-Methyl-4-(5-{[1-(3-nitrophenyl)propyl]thio}-1,3,4-oxadiazol-2-yl)benzyl]amino}propyl)phosphonic acid
3-{[3-Methyl-4-(5-{[1-(3-nitrophenyl)propyl]thio}-1,3,4-oxadiazol-2-yl)benzyl]amino}propanoic acid;
{3-[(4-{5-[(3-Nitrobenzyl)thio]-1,3,4-oxadiazol-2-yl}benzyl)amino]propyl}phosphonic acid;
{3-[(4-{5-[(3,4-Dimethylbenzyl)thio]-1,3,4-oxadiazol-2-yl}benzyl)amino]propyl}phosphonic acid;
(3-{[3-ethyl-4-(5-{[1-(3-Nitrophenyl)ethyl]thio}-1,3,4-oxadiazol-2-yl)benzyl]amino}propyl)phosphonic acid;
(3-{[4-(5-{[1-(3,4-Dimethylphenyl)ethyl]thio}-1,3,4-oxadiazol-2-yl)benzyl]amino}propyl)phosphonic acid;
{3-[(4-{5-[(3-Cyanobenzyl)thio]-1,3,4-oxadiazol-2-yl}benzyl)amino]propyl}phosphonic acid;

{3-[(4-{5-[(1-phenylbutyl)thio]-1,3,4-oxadiazol-2-yl}benzyl)amino]propyl}phosphonic acid;
(3-{[4-(5-{[1-(3-Chloro-2-fluorophenyl)butyl]thio}-1,3,4-oxadiazol-2-yl)benzyl]amino}propyl)phosphonic acid;
(3-{[4-(5-{[1-(3-Nitrophenyl)propyl]thio}-1,3,4-oxadiazol-2-yl)benzyl]amino}propyl)phosphonic acid;
(3-{[4-(5-{[1-(3-nitrophenyl)ethyl]thio}-1,3,4-oxadiazol-2-yl)benzyl]amino}propyl)phosphonic acid;
(3-{[4-(5-{[1-(3-Chloro-2-fluorophenyl)pentyl]thio}-1,3,4-oxadiazol-2-yl)benzyl]amino}propyl)phosphonic acid;
(3-{[4-(5-{[1-(3-Chloro-2-fluorophenyl)hexyl]thio}-1,3,4-oxadiazol-2-yl)benzyl]amino}propyl)phosphonic acid;
(3-{[4-(5-{[1-(3-nitrophenyl)butyl]thio}-1,3,4-oxadiazol-2-yl)benzyl]amino}propyl)phosphonic acid;
(3-{[4-(5-{[1-(3-Bromophenyl)butyl]thio}-1,3,4-oxadiazol-2-yl)benzyl]amino}propyl)phosphonic acid;
(3-((4-(5-((1-(3-Chloro-2-fluorophenyl)heptyl)thio)-1,3,4-oxadiazol-2-yl)benzyl)amino)propyl)phosphonic acid;
3-[(4-{5-[(1-Phenylbutyl)sulfanyl]-1,3,4-oxadiazol-2-yl}benzyl)amino]propanoic acid;
[3-({[4-Methyl-5-(5-{[1-(3-nitrophenyl)ethyl]sulfanyl}-1,3,4-oxadiazol-2-yl)furan-2-yl]methyl}amino)propyl]phosphonic acid;
[3-({[4-Ethyl-5-(5-{[1-(3-nitrophenyl)ethyl]sulfanyl}-1,3,4-oxadiazol-2-yl)furan-2-yl]methyl}amino)propyl]phosphonic acid;
[3-({[4-Ethyl-5-(5-{[1-(3-nitrophenyl)ethyl]sulfanyl}-1,3,4-oxadiazol-2-yl)thiophen-2-yl]methyl}amino)propyl]phosphonic acid;
[3-({[4-Methyl-5-(5-{[1-(3-nitrophenyl)ethyl]sulfanyl}-1,3,4-oxadiazol-2-yl)thiophen-2-yl]methyl}amino)propyl]phosphonic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, such as for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chimica Acta-Zurich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chimica Acta-Zürich, 2002, 329-345).

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, angiogenesis inhibition, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, autoimmune uveitis, renal ischemia/perfusion injury, contact hypersensitivity, atopic dermatitis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or anti-nociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, and individual enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, angiogenesis inhibition, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, autoimmune uveitis, renal ischemia/perfusion injury, contact hypersensitivity, atopic dermatitis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-inoil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene. Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for drop wise application are usually made of suitable inert, non-toxic plastic material, and generally contain between about 0.5 and about 15 ml solution. One package may contain one or more unit doses. Especially preservative-free solutions are often formulated in non-resalable containers containing up to about ten, preferably up to about five units doses, where a typical unit dose is from one to about 8 drops, preferably one to about 3 drops. The volume of one drop usually is about 20-35 ml.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of Formula I according to the invention can be prepared analogously to conventional methods as understood by the person skilled in the art of synthetic organic chemistry. Scheme 1 set forth below, illustrates how compounds according to the invention can be made.

Scheme 1

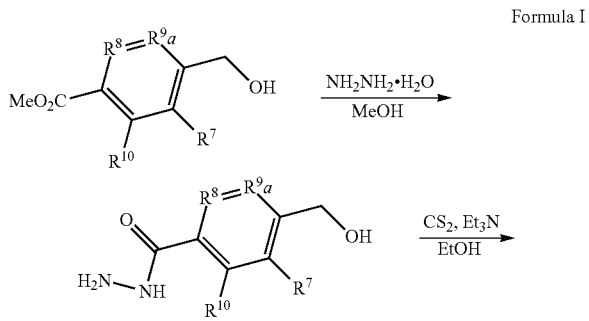

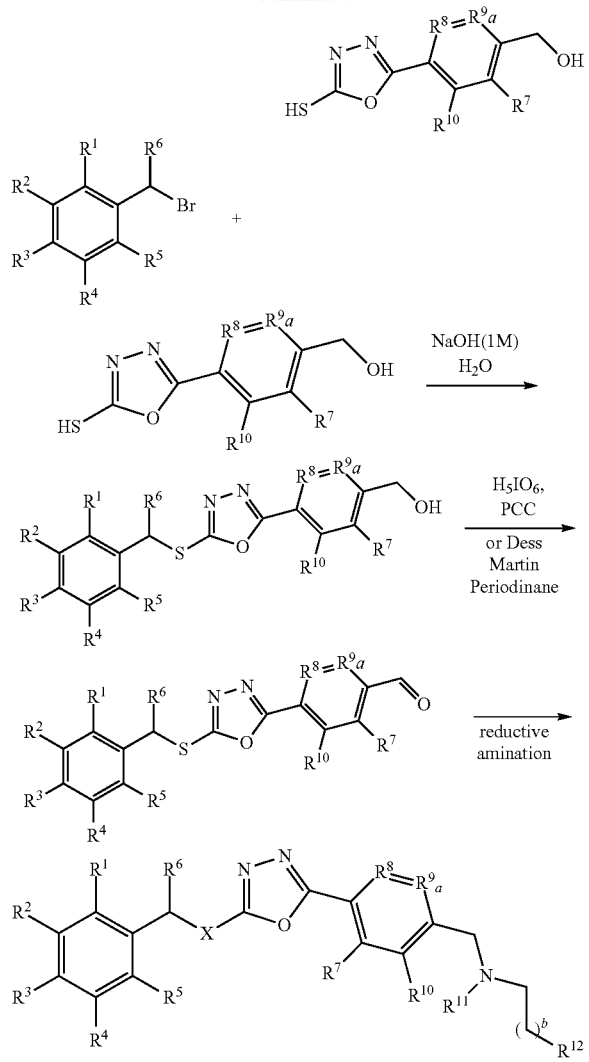

General Procedure

To a solution of 4-hydroxylmethyl benzoic hydrazine in ethanol were added $CS_2$ and $Et_3N$. After heating to reflux for 16 h with stirring, the reaction mixture was diluted with ethyl acetate. The mixture was washed with 10% HCl solution and brine, dried over magnesium sulfate, and concentrated. Purification of the residue by MPLC (65% ethyl acetate in hexanes) the corresponding mercapto oxadiazo intermediate.

To the oxadiazol intermediate in water was added a bromoethylphenyl and sodium hydroxide. After stirring at RT for 16 h, the resulting precipitate was collected by filtration. The solid was dissolved in acetone and purified by MPLC (60% ethyl acetate in hexanes) to afford the corresponding methanol intermediate.

To a solution of periodic acid in acetonitrile (5 mL) which was stirred vigorously for 15 min was added the methanol intermediate at 0° C. followed by pyridinium chlorochromate (2.4 mg, 0.01 mmol). After stirring at 0° C. for 30 min and RT for 30 min, the reaction mixture was diluted with ethyl acetate. The mixture was washed with a 1:1 solution of brine/water, saturated sodium sulfate, and brine, dried over magnesium sulfate, and concentrated. Purification of the residue by MPLC (15% ethyl acetate in hexanes) gave the corresponding aldehyde intermediate.

To a solution of the aldehyde intermediate in methanol were added (3-aminopropyl) phosphonic acid in methanol and tetrabutylammonium hydroxide The reaction mixture was heated to 50° C. for 1 h with stirring, cooled to RT, then sodium borohydride was added. After the reaction mixture was stirred at RT for 3 h, the mixture was concentrated and purified by MPLC (0-100% methanol in ethyl acetate) to give the desired compound of Formula I.

The following abbreviations are used in the examples:

| | |
|---|---|
| MeOH | methanol |
| HCl | hydrochloric acid |
| rt or RT | room temperature |
| $CDCl_3$ | deuterated chloroform |
| $NH_2NH_2 \, H_2O$ | hydrazine |
| $CS_2$ | carbon disulfide |
| $Et_3N$ | thriethylamine |
| EtOH | ethanol |
| NaOH | sodium hydroxide |
| LAH | lithium aluminum hydride |
| $H_5IO_6$ | periodic acid |
| $Bu_4NOH$ | tetrabutylammonium hydroxide |
| $CD_3OD$ | deuterated methanol |
| MPLC | medium pressure liquid chromatography |
| THF | tetrahydrofuran |
| DiBAL | diisobutylaluminum hydride |
| $NaCNBH_3$ | sodium borohydride |
| PPC | pyridinium chlorochromate |

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

Those skilled in the art will be able to routinely modify and/or adapt the following schemes to synthesize any compound of the invention covered by Formula I.

Some compounds of this invention can generally be prepared in one step from commercially available literature starting materials.

As will be evident to those skilled in the art, individual diastereoisomers can be obtained by separation of mixtures thereof in conventional manner, such as chromatographic separation.

Compound names were generated with ACDLabs version 12.5; and intermediates and reagent names used in the examples were generated with software such as Chem Bio Draw Ultra version 12.0 or Auto Nom 2000 from MDL ISIS Draw 2.5 SP1.

In general, characterization of the compounds is performed according to the following methods:

NMR spectra are recorded on 60, 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, AK Scientific, AmFine Com, Carbocore, Maybridge, Frontier, Matrix, Ukrorgsynth, Toronto, Ryan Scientific, Sili-Cycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

Example 1

Intermediate 1

1-(1-bromobutyl)-3-chloro-2-fluorobenzene

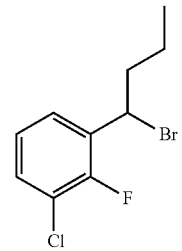

To a solution of 1-(3-chloro-2-fluorophenyl)butan-1-ol (CAS [1340262-68-1], 1.42 g, 7 mmol) in methylene chloride (35 mL) at RT was added triphenylphosphine (2.76 g, 10.5 mmol). After stirring for 15 min, 1,1,1,3,3,3-hexabromoacetone (1.86 g, 3.5 mmol) was added and stirred for 16 h. The reaction mixture was concentrated and the residue was purified by MPLC (100% hexanes) to yield 1.53 g of 1-(1-bromobutyl)-3-chloro-2-fluorobenzene as a colorless oil.

$^1$H NMR (300 MHz, CDCl$_3$) δ 7.39 (ddd, J=1.61, 6.15, 7.91 Hz, 1H), 7.32 (ddd, J=1.47, 6.45, 7.91 Hz, 1H), 7.09 (td, J=1.17, 7.90 Hz, 1H), 5.25 (dd, J=7.33, 7.91 Hz, 1H), 2.20-2.33 (m, 1H), 2.02-2.15 (m, 1H), 1.29-1.60 (m, 2H), 0.95 (t, J=7.33 Hz, 3H)

Intermediates 2 through 5 were prepared from the corresponding starting materials, in a similar manner to the procedure described in Example 1 for Intermediate 1. The results are tabulated below in Table 1.

TABLE 1

| Interm No. | Structure IUPAC name | Starting material | $^1$H NMR δ (ppm) |
|---|---|---|---|
| 2 | 1-(1-bromopentyl)-3-chloro-2-fluorobenzene | CAS [1343222-93-4] 1-(3-chloro-2-fluorophenyl)pentan-1-ol | $^1$H NMR(300 MHz, CDCl$_3$) δ 7.39 (ddd, J = 1.47, 6.45, 7.91 Hz, 1H), 7.32 (ddd, J = 1.76, 6.81, 8.13 Hz, 1H), 7.08 (td, J = 1.47, 7.91 Hz, 1H), 5.23 (dd, J = 7.33, 7.91 Hz, 1H), 2.06-2.34 (m, 2H), 1.21-1.54 (m, 4H), 0.90 (t, J = 7.20 Hz, 3H) |
| 3 | 1-(1-bromohexyl)-3-chloro-2-fluorobenzene | CAS [1341559-62-3] 1-(3-chloro-2-fluorophenyl)hexan-1-ol | $^1$H NMR(300 MHz, CDCl$_3$) δ 7.40 (ddd, J = 1.61, 6.37, 7.84 Hz, 1H), 7.33 (ddd, J = 1.76, 6.74, 8.50 Hz, 1H), 7.10 (td, J = 1.47, 7.91 Hz, 1H), 5.24 (t, J = 7.33 Hz, 1H), 2.04-2.33 (m, 2H), 1.23- 1.55 (m, 6H), 0.88 (t, J = 7.00 Hz, 3H) |

TABLE 1-continued

| Interm No. | Structure IUPAC name | Starting material | $^1$H NMR δ (ppm) |
|---|---|---|---|
| 4 | 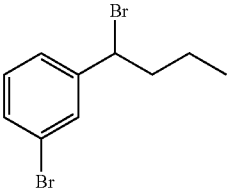<br>1-bromo-3-(1-bromobutyl)benzene | CAS [126342-34-5] 1-(3-bromophenyl) butan-1-ol | $^1$H NMR(300 MHz, CDCl$_3$) δ 7.54 (t, J = 1.76 Hz, 1H), 7.41 (dt, J = 1.47, 7.91 Hz, 1H), 7.31 (d, J = 8.20 Hz, 1H), 7.20 (dd, J = 6.74, 7.33 Hz, 2H), 4.87 (t, J = 7.30 Hz, 1H), 2.00-2.29 (m, 2H), 1.25-1.56 (m, 2H), 0.94 (t, J = 7.47 Hz, 3H) |
| 5 | 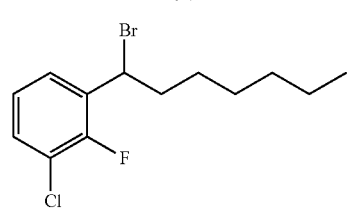 [SMILES: CCCCCCC(Br)c1cccc(Cl)c1F]<br>1-(1-bromoheptyl)-3-chloro-2-fluorobenzene | CAS [1343222-93-4] 1-(3-chloro-2-fluorophenyl) pentan-1-ol | $^1$H NMR(600 MHz, CDCl$_3$) δ:7.38-7.43 (m, 1H), 7.31-7.36 (m, 1H), 7.08-7.14 (m, 1H), 5.22-5.28 (m, 1H), 2.23-2.33 (m, 1H), 2.08- 2.17 (m, 1H), 1.45-1.52 (m, 1H), 1.28 (m, 7H), 0.89 (t, J = 7.0 Hz, 3H) |

Example 2

Intermediate 6

5-Formyl 3-methyl furoic acid

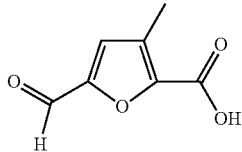

3-Methyl furoic acid (10 g, 79 mmol) and THF (400 mL) n-butyl lithium (67 mL, 0.167 mol) were stirred at a rate sufficient to maintain −70° C. (approx. 1 drop per sec). min then dimethylformamide (30 g, 0.395 mol) was added all at once. The reaction temperature was maintained for an additional 3 hr. After this time the reaction was quenched with the addition of saturated ammonium chloride. The aqueous phase was acidified with 6 N HCl, after extraction and recrystallized from water Intermediate 6 was obtained.

NMR 60 MHz (d$_6$-DMSO) δ 9.0 (s, 1H), 7.4 (s, 1H), 2.5 (s, 3H).

Example 3

Intermediate 7

2-Dimethoxymethyl-4-ethylthiophene

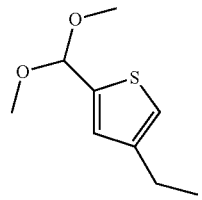

2-Dimethoxymethyl-4-ethynylthiophene (15 g, 0.082 mol) was mixed with 1.5 g Pd[C] in 200 mL of methanol and hydrogenated for 4 hr at 44-31 psi. The mixture was filtered through glass fiber paper and concentrated. The residue (11.6 g) was dissolved in 60 mL of methanol and treated with trimethyl orthoformate (19 g, 0.18 mol) and H$_2$SO$_4$ (6 drops) in a flask equipped with a reflux condenser and drying tube. The mixture was heated at reflux for 70 min, cooled, and poured into 200 mL of saturated aqueous NaHCO$_3$. The suspension was extracted with 200 mL of CH$_2$Cl$_2$, and the organic was filtered through 1 PS paper and concentrated at aspirator pressure. The 16 g of residue was dissolved in 200 mL of hexanes and applied to 150 g of silica gel (topped with Na$_2$SO$_4$ and equilibrated with hexanes).

NMR (60 MHz, d$_6$-DMSO) δ 7.2 (d, 1H), 7.1 (d, 1H), 5.7 (s, 1H), 3.5 (s, 6H), 2.8 (q, 2H), 1.5 (t, 3H).

Example 4

Intermediate 8

Methyl 4-(dimethoxymethyl)benzoate

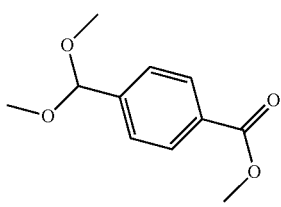

To a solution of methyl 4-formylbenzoate (CAS [1571-08-0] 5.33 g, 32.5 mmol) in methanol (40 mL) were added trimethyl orthoformate (7.5 mL, 68.25 mmol) and sulfuric acid (fuming, 3 drops). After heating to reflux with stirring for 16 h, the reaction mixture was cooled to RT and diluted with methylene chloride. The mixture was washed with a saturated solution of sodium bicarbonate and brine, dried over magnesium sulfate, and concentrated to afford 7 g of methyl 4-(dimethoxymethyl)benzoate as a colorless oil.

¹H NMR (300 MHz, CDCl₃) δ 8.04 (d, J=8.50 Hz, 2H), 7.53 (d, J=8.20 Hz, 2H), 5.44 (s, 1H), 3.92 (s, 3H), 3.33 (s, 6H).

Intermediates 9 through 14 were prepared in a similar manner to the procedure described in Example 4 for Intermediate 8. The results are tabulated below in Table 2.

TABLE 2

| Interm. No. | Structure IUPAC name | Starting material | ¹H NMR δ (ppm) |
|---|---|---|---|
| 9 | Methyl 5-(dimethoxymethyl)-3-methylfuran-2-carboxylate | Interm. 6 | NMR 60 MHz (CDCl₃), δ 6.4 (s, 1 H), 5.4 (s, 1H), 3.9 (S, 3H), 3.4 (s, 6H), 2.3 (s, 3H). |
| 10 | Methyl 4-(dimethoxymethyl)-2-methyl benzoate | 4-formyl-2-methylbenzoic acid | NMR 60 MHz (CDCl₃), δ 7.1-7.8 (m, 3H), 5.3(s, 1H), 3.8 (s, 3H), 3.4 (s, 6H), 2.4 (s, 3H). |
| 11 | Methyl 4-(dimethoxymethyl)-2-ethylbenzoate | 2-ethyl-4-formylbenzoic acid | NMR 60 MHz (CDCl₃), δ 7.2-7.8 (m, 3H), 5.4 (s, 1H), 3.9 (s, 3H), 3.3 (s, 6H), 3.0 (q, 2H), 1.4 (t, 3H) |
| 12 | 5-Dimethoxymethyl-3-methylthiophene-2-carboxylic acid | 5-Formyl-3-methylthiophene-2-carboxylic acid | NMR (60 MHz, CDCl₃) δ 6.8 (s, 1H), 5.5 (s, 1H), 3.8 (s, 3H), 3.3 (s, 6H). 2.5 (s, 3H). |
| 13 | Methyl 5-dimethoxymethyl-3-ethylthiophene-2-carboxylate | Interm. 7 | NMR (60 MHz, CDCl₃) δ 6.8 (s, 1H), 5.5 (s, 1H), 3.8 (s, 3H), 3.3 (s, 6H), 3.0 (q, 2H), 1.2 (t, 3H). |
| 14 | Methyl 5-(dimethoxymethyl)-3-ethylfuran-2-carboxylate | 3-ethyl-2-furancarboxylic acid CAS [704913-85-9] | NMR 60 MHz (CDCl₃), δ 6.4 (s, 1H), 5.4 (s, 1H), 3.8 (s. 3H), 3.4 (s, 6H), 2.8 (qj = 8Hz, 2H), 1.2 (t j = 8Hz, 3H). |

Example 5

Intermediate 15

4-(Dimethoxymethyl)benzohydrazide

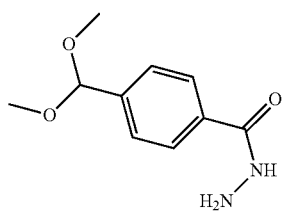

A solution of Intermediate 8 (7 g, 32.5 mmol) in hydrazine hydrate (7.9 mL) was heated to 100° C. with stirring for 2 h. The reaction mixture was cooled to RT and diluted with dichloromethane. The mixture was washed with water and brine, dried over magnesium sulfate, and concentrated to give rise to 6.2 g of 4-(dimethoxy methyl)benzohydrazide as a colorless solid.

$^1$H NMR (300 MHz, Acetone-$d_6$) δ 7.86 (d, J=8.20 Hz, 2H), 7.48 (d, J=8.50 Hz, 2H), 5.44 (s, 1H), 3.30 (s, 6H)

Intermediates 16 through 21 were prepared in a similar manner to the procedure described in Example 5 for Intermediate 15, starting from the corresponding intermediate. The results are tabulated below in Table 3.

TABLE 3

| Interm. No. | Structure IUPAC name | Intermediate Number | $^1$H NMR δ (ppm) |
|---|---|---|---|
| 16 | N-amino 5-(dimethoxymethyl)-3-methylfuran-2-carboxamide | 9 | NMR 60 MHz ($D_6$ DMSO), δ 6.9 (s, 1H), 5.9 (s, 1H), 4.9 (s, 1H), 3.9 (s, 6H), 2.8 (s, 3H). |
| 17 | N-amino[4-(dimethoxymethyl)-2-methylphenyl]carboxamide | 10 | NMR 60 MHz (CDCl$_3$), δ 7.6 (brs, 1H), 7.3 (s, 3H), 5.3 (s, 1H), 3.5 (brs, 2H), 3.3 (s, 6H), 2.4 (s, 3H). |
| 18 | N-amino[4-(dimethoxymethyl)-2-ethylphenyl]carboxamide | 11 | NMR 60 MHz (CDCl$_3$), δ 7.1-7.4 (m, 3H), 5.3 (s, 1H), 4.0 (brs, 3H), 3.3 (s, 6H), 2.7 (q, 2H), 1.2 (t, 3H) |
| 19 | 5-Dimethoxymethyl-3-methylthiophene-2-carboxylic acid hydrazide | 12 | NMR (60 MHz, CDCl$_3$/CD$_3$OD) δ 6.8 (s, 1H), 5.5 (s, 1H), 3.8 (bs, 10H (exchangeable protons-still wet with water)), 3.3 (s, 6H), 2.5 (s, 3 H). |

TABLE 3-continued

| Interm. No. | Structure IUPAC name | Intermediate Number | $^1$H NMR δ (ppm) |
|---|---|---|---|
| 20 | 5-Dimethoxymethyl-3-ethylthiophene-2-carboxylic acid hydrazide | 13 | NMR (60 MHz, CDCl$_3$) δ 6.8 (s, 1H), 5.5 (s, 1H), 4.1 (bs, 3H), 3.3 (s, 6H), 2.9 (q, 2H), 1.2 (t, 3H). |
| 21 | N-amino 5-(dimethoxymethyl)-3-ethylfuran-2-carboxamide | 14 | NMR 60 MHz (CDCl$_3$), δ 7.8 (br s, 1H), 6.3 (s, 1H), 5.2 (s, 1H), 4.0 (br s, 2H), 3.3 (s, 6H), 2.8 (q j = 8 Hz, 2H), 1.2 (t j = 8 Hz, 3H). |

Example 6

Intermediate 22

[4-(5-Mercapto-1,3,4-oxadiazol-2-yl)phenyl]methanol

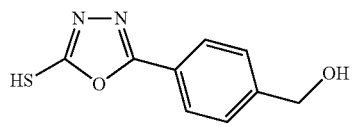 [SMILES: OCc1ccc(-c2nnc(S)o2)cc1]

To a solution of 4-(hydroxymethyl)benzoic hydrazide CAS [58855-42-8] (1.4 g, 8.4 mmol) in ethanol (14 mL) were added carbon disulfide (1.12 mL, 18.5 mmol) and triethyl amine (1.3 mL, 9.3 mmol). After heating to reflux for 16 h with stirring, the reaction mixture was cooled to RT and diluted with ethyl acetate. The mixture was washed with 10% HCl solution and brine, dried over magnesium sulfate, and concentrated. Purification of the residue by MPLC (65% ethyl acetate in hexanes) gave 1.62 g of [4-(5-mercapto-1,3,4-oxadiazol-2-yl)phenyl]methanol as a colorless solid. $^1$H NMR (600 MHz, CD$_3$OD) δ 7.90 (ddd, J=0.59, 2.05, 8.51 Hz, 2H), 7.54 (d, J=7.92 Hz, 2H), 4.68 (s, 2H)

Intermediate 23 through 29 were prepared in a similar manner to the procedure described in Example 6 for Intermediate 22, staring from the corresponding intermediate. The results are tabulated below in Table 4.

TABLE 4

| Interm. No. | Structure IUPAC name | Intermediate Number | $^1$H NMR δ (ppm) |
|---|---|---|---|
| 23 | 5-[4-(Dimethoxymethyl)phenyl]-1,3,4-oxadiazole-2-thiol | 22 | $^1$H NMR (300 MHz, Acetone-d$_6$) δ 7.88 (d, J = 8.20 Hz, 2H), 7.50 (d, J = 8.20 Hz, 2H), 5.43 (s, 1H), 3.29 (s, 6H) |
| 24 | 5-(5-(Dimethoxymethyl)-3-methylfuran-2-yl)-1,3,4-oxadiazole-2-thiol | 16 | NMR 60 MHz (CDCl$_3$), δ 6.4 (s, 1H), 5.4 (s, 1H), 4.4 (s, 1H), 3.4 (s, 6H), 2.3 (s, 3H). |

TABLE 4-continued

| Interm. No. | Structure IUPAC name | Intermediate Number | $^1$H NMR δ (ppm) |
| --- | --- | --- | --- |
| 25 | 5-[4-(Dimethoxymethyl)-2-methylphenyl]-1,3,4-oxadiazole-2-thiol | 17 | NMR 60 MHz (CDCl$_3$), δ 7.2-7.9 (m, 3H), 5.4 (s, 1H), 3.3 (s, 6H), 2.6 (s, 3H). |
| 26 | 5-[4-(Dimethoxymethyl)-2-ethylphenyl]-1,3,4-oxadiazole-2-thiol | 18 | NMR 60 MHz (CDCl$_3$), δ 7.2-7.7 (m, 3H), 5.4 (s, 1H), 3.4 (s, 6H), 3.0 (q, 2H), 1.3 (t, 3H). |
| 27 | 2-Dimethoxymethyl-4-methyl-5-(5-mercapto-1,3,4-oxadiazol-2-yl)thiophene | 19 | NMR (60 MHz, CDCl$_3$/CD$_3$OD) δ 6.8 (s, 1H), 5.5 (s, 1H), 4.6 (bs, 4H (still contains EtOH)), 3.3 (s, 6H), 2.5 (s, 3 H). |
| 28 | 2-Dimethoxymethyl-4-ethyl-5-(5-mercapto-1,3,4-oxadiazol-2-yl)thiophene | 20 | NMR (60 MHz, d$_6$-DMSO) δ 7.4 (bs, 3H (xs)), 7.0 (s, 1H), 5.6 (s, 1H), 3.3 (s, 6H), 2.9 (q, 2H), 1.2 (t, 3H). |
| 29 | 5-(5-(dimethoxymethyl)-3-ethylfuran-2-yl)-1,3,4-oxadiazole-2-thiol | 21 | NMR 60 MHz (CDCl$_3$), δ 9.5 (br s, 1H), 6.5 (s, 1H), 5.4 (s, 1H), 3.3 (s, 6H), 2.7 (q j = 6 Hz, 2H), 1.2 (t j = 6 Hz, 3H). |

Example 7

Intermediate 30

(4-{5-[(3-Chloro-2-fluorobenzyl)thio]-1,3,4-oxadiazol-2-yl}phenyl)methanol

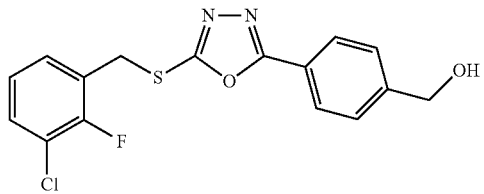 [SMILES: OCc1ccc(-c2nnc(SCc3cccc(Cl)c3F)o2)cc1]

To a solution of Intermediate 22 (596 mg, 2.86 mmol) and 1-(bromomethyl)-3-chloro-2-fluorobenzene (CAS [85070-47-9] 639 mg, 2.86 mmol) in water (13 mL) was added NaOH (1 M, 3.2 mL). After stirring at RT for 16 h, the resulting precipitate was collected by filtration. The solid was dissolved in acetone and purified by MPLC (60% ethyl acetate in hexanes) to afford 703 mg of 4-{5-[(3-chloro-2-fluorobenzyl)thio]-1,3,4-oxadiazol-2-yl}phenyl)methanol as a colorless solid.

$^1$H NMR (600 MHz, CDCl$_3$) δ 7.97 (d, J=8.22 Hz, 2H), 7.48 (s, 1H), 7.48 (ddd, J=1.76, 6.16, 8.22 Hz, 1H), 7.35 (ddd, J=1.17, 6.75, 8.80 Hz, 1H), 7.05 (td, J=0.88, 7.92 Hz, 1H), 4.78 (d, J=5.58 Hz, 2H), 4.54 (d, J=0.59 Hz, 2H), 2.01 (t, J=5.87 Hz, 1H).

Intermediates 31 through 50 were prepared from the corresponding starting materials, in a similar manner to the procedure described in Example 7 for Intermediate 30. The results are tabulated below in Table 5.

TABLE 5

| Interm. No. | Structure IUPAC name | Starting materials | $^1$H NMR δ (ppm) |
|---|---|---|---|
| 31 | (4-{5-[(3-nitrobenzyl)thio]-1,3,4-oxadiazol-2-yl}phenyl)methanol | Interm. 22 CAS [3958-57-4] 3-nitrobenzyl bromide | $^1$H NMR (300 MHz, CDCl$_3$) δ 8.36 (t, J = 1.76 Hz, 1H), 8.16 (dd, J = 1.17, 8.20 Hz, 1H), 7.97 (d, J = 8.20 Hz, 2H), 7.87 (d, J = 8.20 Hz, 1H), 7.47-7.56 (m, 3H), 4.78 (d, J = 4.69 Hz, 2H), 4.59 (s, 2H), 1.81 (br. s., 1H) |
| 32 | (4-{5-[(3,4-dimethylbenzyl)thio]-1,3,4-oxadiazol-2-yl}phenyl)methanol | Interm. 22 CAS [94416-66-7] 4-(bromomethyl)-1,2-dimethylbenzene | $^1$H NMR (300 MHz, CDCl$_3$) δ 7.98 (d, J = 8.20 Hz, 2H), 7.49 (d, J = 8.79 Hz, 2H), 7.22 (s, 1H), 7.18 (dd, J = 2.05, 9.67 Hz, 1H), 7.10 (d, J = 7.91 Hz, 1H), 4.78 (d, J = 5.27 Hz, 2H), 4.48 (s, 2H), 2.26 (s, 3H), 2.24 (s, 3H) |
| 33 | [4-(5-{[1-(3,4-dimethylphenyl)ethyl]thio}-1,3,4-oxadiazol-2-yl)phenyl]methanol | Interm. 22 CAS [20871-94-7] 4-(1-bromoethyl)-1,2-dimethylbenzene | $^1$H NMR (300 MHz, CDCl$_3$) δ 7.96 (d, J = 8.20 Hz, 2H), 7.48 (dd, J = 0.59, 7.91 Hz, 2H), 7.15-7.22 (m, 2H), 7.10 (d, J = 7.33 Hz, 1H), 4.98 (q, J = 7.03 Hz, 1H), 4.78 (d, J = 5.27 Hz, 2H), 2.25 (s, 3H), 2.23 (s, 3H), 1.85 (d, J = 7.03 Hz, 3H) |
| 34 | 3-[({5-[4-(hydroxymethyl)phenyl]-1,3,4-oxadiazol-2-yl}thio)methyl]benzonitrile | Interm 22 CAS [28188-1-2] 3-(bromomethyl)-benzonitrile | $^1$H NMR (300 MHz, Acetone-d$_6$) δ 7.90-8.00 (m, 4H), 7.72 (dt, J = 1.17, 7.91 Hz, 1H), 7.61 (d, J = 7.91 Hz, 1H), 7.55-7.59 (m, 2H), 4.74 (d, J = 5.57 Hz, 2H), 4.68 (s, 2H) |

TABLE 5-continued

| Interm. No. | Structure IUPAC name | Starting materials | $^1$H NMR δ (ppm) |
|---|---|---|---|
| 35 | 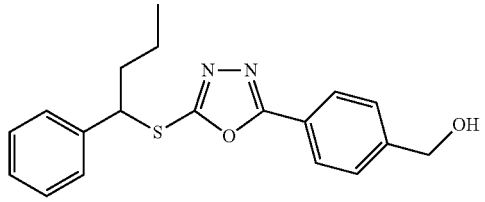 [SMILES: CCCC(Sc1nnc(-c2ccc(CO)cc2)o1)c1ccccc1]<br>(4-{5-[(1-phenylbutyl)thio]-1,3,4-oxadiazol-2-yl}phenyl)methanol | Interm. 22<br>(1-Bromobutyl) benzene CAS [53118-87-9] | $^1$H NMR (300 MHz, CDCl$_3$) δ 7.90 (d, J = 8.50 Hz, 2H), 7.46 (d, J = 8.50 Hz, 2H), 7.41 (dd, J = 1.76, 8.50 Hz, 2H), 7.24-7.35 (m, 3H), 4.83 (dd, J = 6.45, 8.79 Hz, 1H), 4.76 (s, 2H), 1.99-2.23 (m, 2H), 1.25-1.49 (m, 2H), 0.93 (t, J = 7.33 Hz, 3H) |
| 36 | 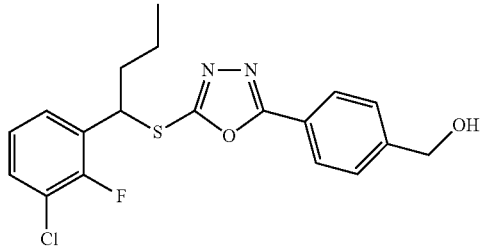 [SMILES: CCCC(Sc1nnc(-c2ccc(CO)cc2)o1)c1cccc(Cl)c1F]<br>[4-(5-{[1-(3-chloro-2-fluorophenyl)butyl]thio}-1,3,4-oxadiazol-2-yl)phenyl]methanol | Interm. 22<br>Interm. 1 | $^1$H NMR (300 MHz, CDCl$_3$) δ 7.89 (d, J = 8.20 Hz, 2H), 7.46 (d, J = 8.50 Hz, 2H), 7.38 (ddd, J = 1.47, 6.15, 7.62 Hz, 1H), 7.27-7.33 (m, 1H), 7.06 (td, J = 1.03, 7.84 Hz, 1H), 5.10 (dd, J = 7.03, 8.50 Hz, 0H), 4.76 (s, 2H), 1.99-2.23 (m, 2H), 1.30-1.53 (m, 2H), 0.96 (t, J = 7.33 Hz, 2H) |
| 37 | 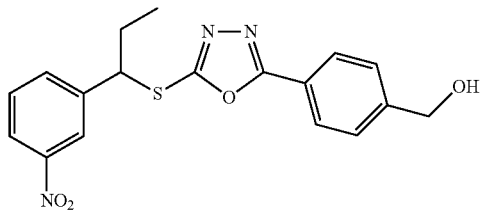 [SMILES: CCC(Sc1nnc(-c2ccc(CO)cc2)o1)c1cccc([N+](=O)[O-])c1]<br>[4-(5{[1-(3-nitrophenyl)propyl]thio}-1,3,4-oxadiazol-2-yl)phenyl]methanol | Interm. 22<br>CAS [29067-56-9]<br>1-(1-bromopropyl)-3-nitrobenzene | $^1$H NMR (300 MHz, CDCl$_3$) δ 8.32 (t, J = 1.90 Hz, 1H), 8.13 (ddd, J = 1.17, 2.27, 8.28 Hz, 1H), 7.90-7.94 (m, 2H), 7.80 (dt, J = 1.47, 7.62 Hz, 1H), 7.45-7.54 (m, 3H), 4.85 (dd, J = 7.03, 8.50 Hz, 1H), 4.77 (d, J = 5.57 Hz, 2H), 2.06-2.33 (m, 2H), 1.98 (t, J = 5.86 Hz, 1H), 1.05 (t, J = 7.33 Hz, 3H) |
| 38 | 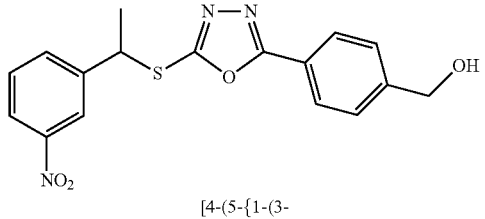<br>[4-(5-{1-(3-nitrophenyl)ethyl]thio}-1,3,4-oxadiazol-2-yl)phenyl]methanol | Interm. 22<br>CAS [29067-55-8]<br>1-(1-bromoethyl)-3-nitrobenzene | $^1$H NMR (300 MHz, CDCl$_3$) δ 8.36 (t, J = 1.90 Hz, 1H), 8.13 (ddd, J = 0.90, 2.05, 8.20 Hz, 1H), 7.92 (d, J = 8.20 Hz, 2H), 7.84 (d, J = 7.91 Hz, 1H), 7.53 (d, J = 7.91 Hz, 1H), 7.47 (d, J = 8.20 Hz, 2H), 5.11 (q, J = 7.03 Hz, 1H), 4.77 (d, J = 5.57 Hz, 2H), 2.28 (t, J = 5.86 Hz, 1H), 1.89 (d, J = 7.03 Hz, 3H) |
| 39 | 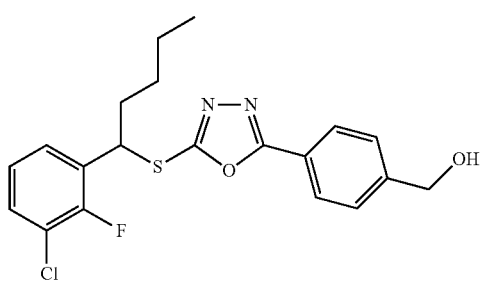 [SMILES: CCCCC(Sc1nnc(-c2ccc(CO)cc2)o1)c1cccc(Cl)c1F]<br>[4-(5-{[1-(3-chloro-2-fluorophenyl)pentyl]thio}-1,3,4-oxadiazol-2-yl)phenyl]methanol | Interm. 22<br>Interm. 2 | $^1$H NMR (300 MHz, CDCl$_3$) δ 7.92 (d, J = 8.20 Hz, 2H), 7.47 (d, J = 8.50 Hz, 2H), 7.38 (ddd, J = 1.47, 6.45, 8.20 Hz, 1H), 7.31 (ddd, J = 1.76, 6.81, 8.13 Hz, 1H), 7.06 (ddd, J = 1.17, 7.62, 8.20 Hz, 1H), 5.08 (dd, J = 7.03, 8.50 Hz, 1H), 4.77 (d, J = 4.98 Hz, 2H), 2.01-2.26 (m, 2H), 1.66 (s, 1H), 1.25-1.49 (m, 4H), 0.89 (t, J = 7.33 Hz, 3H) |

TABLE 5-continued

| Interm. No. | Structure IUPAC name | Starting materials | $^1$H NMR δ (ppm) |
|---|---|---|---|
| 40 | 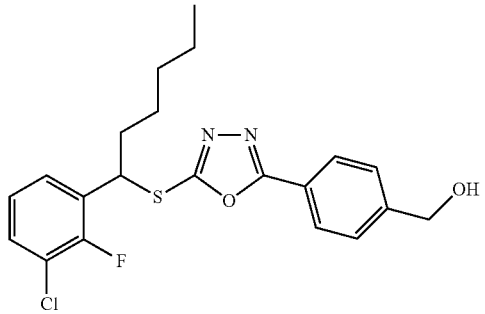 [SMILES: CCCCCC(Sc1nnc(-c2ccc(CO)cc2)o1)c1cccc(Cl)c1F]<br>[4-(5-{[1-(3-chloro-2-fluorophenyl)hexyl]thio}-1,3,4-oxadiazol-2-yl)phenyl]methanol | Interm. 22<br>Interm. 3 | $^1$H NMR (300 MHz, CDCl$_3$) δ 7.87 (d, J = 8.20 Hz, 2H), 7.45 (d, J = 8.50 Hz, 2H), 7.37 (ddd, J = 1.47, 6.45, 7.62 Hz, 1H), 7.30 (ddd, J = 1.76, 6.45, 8.20 Hz, 1H), 7.05 (td, J = 0.88, 7.91 Hz, 1H), 5.08 (dd, J = 6.89, 8.64 Hz, 1H), 4.75 (s, 2H), 2.97 (br. s., 1H), 2.00-2.25 (m, 2H), 1.24-1.49 (m, 6H), 0.86 (t, J = 7.20 Hz, 3H) |
| 41 | 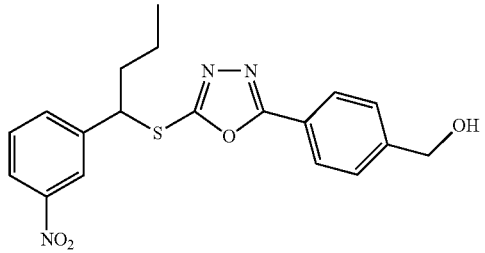 [SMILES: CCCC(Sc1nnc(-c2ccc(CO)cc2)o1)c1cccc([N+](=O)[O-])c1]<br>[4-(5-{[1-(3-nitrophenyl)butyl]thio}-1,3,4-oxadiazol-2-yl)phenyl]methanol | Interm. 22<br>CAS [29067-57-0]<br>1-(1-bromobutyl)-3-nitrobenzene | $^1$H NMR (300 MHz, CDCl$_3$) δ 8.33 (t, J = 1.90 Hz, 1H), 8.11 (ddd, J = 1.20, 2.34, 8.20 Hz, 1H), 7.90 (d, J = 8.50 Hz, 2H), 7.81 (d, J = 7.91 Hz, 1H), 7.51 (d, J = 8.20 Hz, 1H), 7.46 (d, J = 7.91 Hz, 2H), 4.93 (dd, J = 7.18, 8.35 Hz, 1H), 4.76 (d, J = 4.69 Hz, 2H), 1.99-2.25 (m, 2H), 1.31-1.55 (m, 2H), 0.97 (t, J = 7.33 Hz, 3H) |
| 42 | 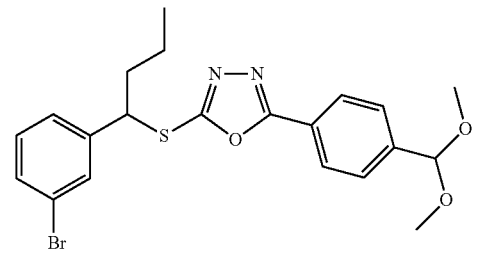 [SMILES: CCCC(Sc1nnc(-c2ccc(C(OC)OC)cc2)o1)c1cccc(Br)c1]<br>2-{[1-(3-bromophenyl)butyl]thio}-5-[4-(dimethoxymethyl)phenyl]-1,3,4-oxadiazole | Interm. 22<br>Interm. 4 | $^1$H NMR (300 MHz, CDCl$_3$) δ 7.95 (d, J = 8.50 Hz, 2H), 7.55-7.59 (m, 3H), 7.34-7.41 (m, 2H), 7.19 (t, J = 7.91 Hz, 1H), 5.44 (s, 1H), 4.78 (dd, J = 7.03, 8.50 Hz, 1H), 3.34 (s, 6H), 1.94-2.20 (m, 2H), 1.23-1.50 (m, 2H), 0.95 (t, J = 7.33 Hz, 3H) |
| 43 | 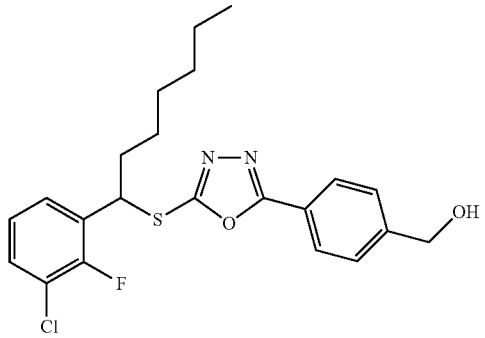 [SMILES: CCCCCCC(Sc1nnc(-c2ccc(CO)cc2)o1)c1cccc(Cl)c1F]<br>(4-(5-((1-(3-chloro-2-fluorophenyl)heptyl)thio)-1,3,4-oxadiazol-2-yl)phenyl)methanol | Interm. 22<br>Interm. 5 | $^1$H NMR (600 MHz, CDCl$_3$) δ: 7.94 (d, J = 8.4 Hz, 2H), 7.49 (d, J = 8.5 Hz, 2H), 7.36-7.41 (m, 1H), 7.29-7.34 (m, 1H), 7.04-7.09 (m, 1H), 5.06-5.12 (m, 1H), 4.78 (m, 2H), 2.15-2.24 (m, 1H), 2.03-2.13 (m, 1H), 1.41-1.49 (m, 1H), 1.20-1.38 (m, 7H), 0.87 (t, J = 7.0 Hz, 3H) |

TABLE 5-continued

| Interm. No. | Structure IUPAC name | Starting materials | $^1$H NMR δ (ppm) |
|---|---|---|---|
| 44 | 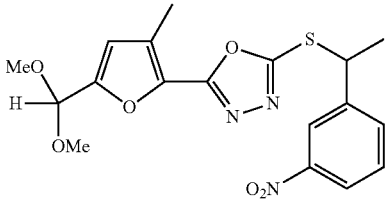 [SMILES: COC(OC)c1cc(C)c(-c2nnc(SC(C)c3cccc([N+](=O)[O-])c3)o2)o1]  2-dimethoxymethyl-4-methyl-5-(5-{[1-(3-nitrophenyl)ethyl]thio}-1,3,4-oxadiazol-2-yl)-furan | Interm. 24 1-(1-Bromoethyl)-3-nitrobenzene CAS [29067-55-8] | NMR 60 MHz (CDCl$_3$), δ 8.1-7.2 (m, 5H), 6.3 (s, 1H), 5.3 (s, 1H), 5.0 (q j = 6 Hz, 1H), 3.3 (s, 6H), 2.4 (s, 3H), 1.9 (d j = 6 Hz, 3H). |
| 45 | 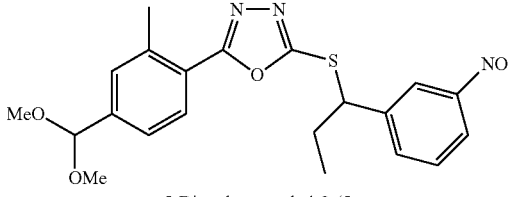  5-Dimethoxymethyl-2-(5-{[1-(3-nitriphenol)propyl]thio}-1,3,4-oxadiazol-2-yl)toluene | Interm. 25 3-(bromopropyl)-1-nitrobenzene CAS [29067-56-9] | NMR 60 MHz (CDCl$_3$), δ, 7.2-8.2 (m, 7H), 5.3 (s, 1H), 4.8 (t, 1H), 3.3 (s, 6H), 2.7 (s, 3H), 1.8-2.5 (m, 2H), 1.0 (t, 3H). |
| 46 | 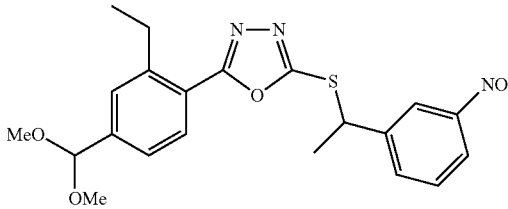  (3-Ethyl-4-{(5-[(3-nitrophenyl)ethylthio](1,3,4-oxadiazol-2-yl}phenyl)dimethoxymethane | Interm. 26 1-(1-Bromoethyl)-3-nitrobenzene CAS [29067-55-8] | NMR 60 MHz (CDCl$_3$), δ, 7.1-8.3 (m, 7H), 5.3 (s, 1H), 5.0 (q, 1H), 3.3 (s, 6H), 3.0 (q, 2H), 1.9 (d, 3H), 1.3 (t, 3H). |
| 47 | 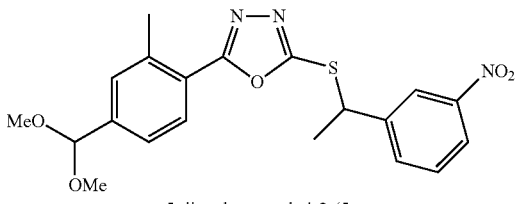  5-dimethoxymethyl-2-(5-{[1-(3-nitriphenol)ethyl]thio}-1,3,4-oxadiazol-2-yl)toluene | Interm. 25 1-(1-Bromoethyl)-3-nitrobenzene CAS [29067-55-8] | NMR 60 MHz (CDCl$_3$), δ, 7.2-8.2 (m, 7H), 5.3 (s, 1H), 5.1 (q, 1H), 3.3 (s, 6H), 2.6 (s, 3H), 1.9 (d, 3H). |
| 48 | 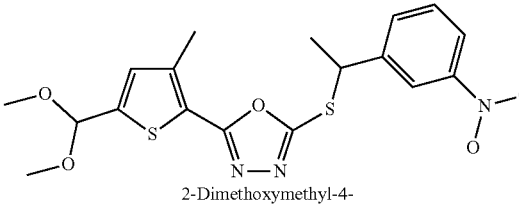  2-Dimethoxymethyl-4-methyl-5-(5-{[1-(3-nitrophenyl)ethyl]thio}-1,3,4-oxadiazol-2-yl)thiophene | Interm. 27 1-(1-Bromoethyl)-3-nitrobenzene CAS [29067-55-8] | NMR (60 MHz, CDCl$_3$/CD$_3$OD) δ 6.8-8.3 (m, 5H), 5.5 (1H), 5.0 (q, 1H), 3.3 (s, 6H), 2.5 (s, 3 H), 1.9 (d, 3H). |

TABLE 5-continued

| Interm. No. | Structure IUPAC name | Starting materials | $^1$H NMR δ (ppm) |
|---|---|---|---|
| 49 | 2-Dimethoxymethyl-4-ethyl-5-(5-{[1-(3-nitrophenyl)ethyl]thio}-1,3,4-oxadiazol-2-yl)thiophene | Interm. 28 1-(1-Bromoethyl)-3-nitrobenzene CAS [29067-55-8] | NMR (60 MHz, CDCl$_3$) δ 7.2-8.3 (m, 4H), 6.9 (s, 1H), 5.5 (1H), 5.0 (q, 1H), 3.3 (s, 6H), 2.9 (q, 2H), 1.9 (d, 3 H), 1.2 (t, 3H). |
| 50 | 2-Dimethoxymethyl-4-ethyl-5-(5-{[1-(3-nitrophenyl)ethyl]thiol}-1,3,4-oxadiazol-2-yl)-furan | Interm. 29 1-(1-Bromoethyl)-3-nitrobenzene CAS [29067-55-8] | NMR 60 MHz (CDCl$_3$), δ 8.2-7.0 (m, 4H), 6.4 (s, 1H), 5.3 (s, 1H), 5.0 (q j = 6 Hz, 1H), 3.3 (s, 6H), 2.7 (q j = 8 Hz, 2H), 1.9 (d j = 6 Hz, 3H),1.2 (t j = 8 Hz, 3H). |

Example 8

Intermediate 51

4-{5-[(3-chloro-2-fluorobenzyl)thio]-1,3,4-oxadiazol-2-yl}benzaldehyde

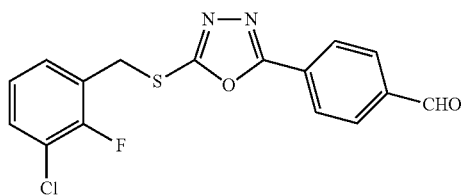 [SMILES: O=Cc1ccc(-c2nnc(SCc3cccc(Cl)c3F)o2)cc1]

To a solution of periodic acid (137 mg, 0.6 mmol) in acetonitrile (5 mL) that was stirred vigorously for 15 min was added Intermediate 30 (200 mg, 0.57 mmol) at 0° C. followed by pyridinium chlorochromate (2.4 mg, 0.01 mmol). After stirring at 0° C. for 30 min and RT for 30 min, the reaction mixture was diluted with ethyl acetate. The mixture was washed with a 1:1 solution of brine/water, saturated sodium sulfate, and brine, dried over magnesium sulfate, and concentrated. Purification of the residue by MPLC (15% ethyl acetate in hexanes) gave rise to 149 mg of 4-{5-[(3-chloro-2-fluorobenzyl)thio]-1,3,4-oxadiazol-2-yl}benzaldehyde as a colorless solid.

$^1$H NMR (300 MHz, CDCl$_3$) δ 10.09 (s, 1H), 8.17 (d, J=8.20 Hz, 2H), 8.01 (d, J=7.91 Hz, 2H), 7.49 (t, J=6.59 Hz, 1H), 7.36 (t, J=7.91 Hz, 1H), 7.06 (t, J=7.76 Hz, 1H), 4.58 (s, 2H).

Intermediates 52 through 70 were prepared from the corresponding Intermediate, in a similar manner to the procedure described in Example 8 for Intermediate 51. The results are tabulated below in Table 6.

TABLE 6

| Interm. No. | Structure IUPAC name | Interm. No. | $^1$H NMR δ (ppm) |
|---|---|---|---|
| 52 | 4-{5-[(3-nitrobenzyl)thio]-1,3,4-oxadiazol-2-yl}benzaldehyde | 31 | $^1$H NMR (300 MHz, CDCl$_3$) δ 10.09 (s, 1H), 8.37 (t, J = 1.90 Hz, 1H), 8.14-8.19 (m, 1H), 8.16 (d, J = 8.50 Hz, 2H), 8.01 (d, J = 8.50 Hz, 2H), 7.99-8.03 (m, 1H), 7.88 (ddd, J = 1.03, 1.17, 7.77 Hz, 1H), 4.62 (s, 2H) |

TABLE 6-continued

| Interm. No. | Structure  IUPAC name | Interm. No. | ¹H NMR δ (ppm) |
|---|---|---|---|
| 53 | 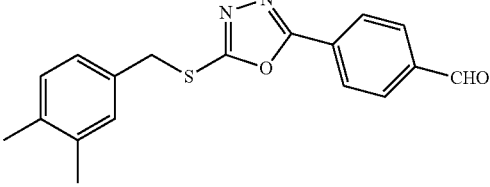  4-{5-[(3,4-dimethylbenzyl)thio]-1,3,4-oxadiazol-2-yl}benzaldehyde | 32 | ¹H NMR (300 MHz, CDCl$_3$) δ 10.09 (s, 1H), 8.17 (d, J = 8.20 Hz, 2H), 8.01 (d, J = 8.79 Hz, 2H), 7.17-7.23 (m, 2H), 7.11 (d, J = 8.20 Hz, 1H), 4.50 (s, 2H), 2.26 (s, 3H), 2.24 (s, 3H) |
| 54 | 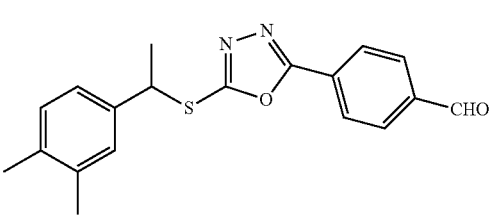 [SMILES: Cc1ccc(C(C)Sc2nnc(-c3ccc(C=O)cc3)o2)cc1C]  4-(5-{[1-(3,4-dimethylphenyl)ethyl]thio}-1,3,4-oxadiazol-2-yl)benzaldehyde | 33 | ¹H NMR (300 MHz, CDCl$_3$) δ 10.08 (s, 1H), 8.15 (d, J = 8.20 Hz, 2H), 8.00 (d, J = 8.50 Hz, 2H), 7.16-7.23 (m, 2H), 7.11 (d, J = 7.62 Hz, 1H), 5.02 (q, J = 7.00 Hz, 1H), 2.26 (s, 3H), 2.24 (s, 3H), 1.87 (d, J = 7.03 Hz, 3H) |
| 55 | 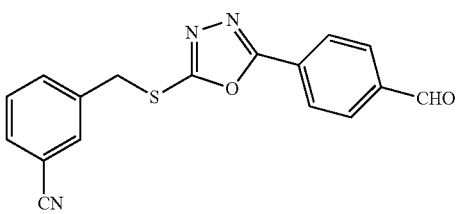 [SMILES: N#Cc1cccc(CSc2nnc(-c3ccc(C=O)cc3)o2)c1]  3-({[5-(4-formylphenyl)-1,3,4-oxadiazol-2-yl]thio}methyl)benzonitrile | 34 | ¹H NMR (300 MHz, CDCl$_3$) δ 10.09 (s, 1H), 8.16 (d, J = 8.50 Hz, 2H), 8.01 (d, J = 8.79 Hz, 2H), 7.81 (s, 1H), 7.76 (d, J = 7.91 Hz, 1H), 7.60 (d, J = 7.91 Hz, 1H), 7.47 (t, J = 7.62 Hz, 1H), 4.55 (s, 2H) |
| 56 | 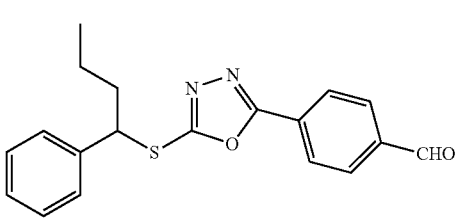 [SMILES: CCCC(Sc1nnc(-c2ccc(C=O)cc2)o1)c1ccccc1]  4-{5-[(1-phenylbutyl)thio]-1,3,4-oxadiazol-2-yl}benzaldehyde | 35 | ¹H NMR (300 MHz, CDCl$_3$) δ 10.08 (s, 1H), 8.12 (d, J = 8.20 Hz, 2H), 7.99 (d, J = 8.20 Hz, 2H), 7.43 (d, J = 6.74 Hz, 2H), 7.23-7.36 (m, 3H), 4.88 (dd, J = 6.45, 9.08 Hz, 1H), 2.01-2.26 (m, 2H), 1.31-1.50 (m, 2H), 0.94 (t, J = 7.33 Hz, 3H) |
| 57 | 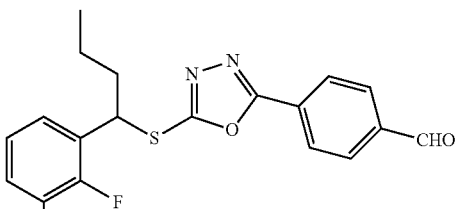  4-(5-{[1-(3-chloro-2-fluorophenyl)butyl]thio}-1,3,4-oxadiazol-2-yl)benzaldehyde | 36 | ¹H NMR (300 MHz, CDCl$_3$) δ 10.08 (s, 1H), 8.12 (d, J = 8.20 Hz, 2H), 8.00 (d, J = 8.50 Hz, 2H), 7.40 (ddd, J = 1.47, 7.03, 7.91 Hz, 1H), 7.32 (ddd, J = 1.17, 7.03, 8.20 Hz, 1H), 7.08 (td, J = 0.88, 7.91 Hz, 1H), 5.15 (dd, J = 7.03, 8.79 Hz, 1H), 2.02-2.26 (m, 2H), 1.32-1.55 (m, 2H), 0.97 (t, J = 7.47 Hz, 3H) |

TABLE 6-continued

| Interm. No. | Structure / IUPAC name | Interm. No. | ¹H NMR δ (ppm) |
|---|---|---|---|
| 58 | 4-(5-{[1-(3-nitrophenyl)propyl]thio}-1,3,4-oxadiazol-2-yl)benzaldehyde | 37 | ¹H NMR (300 MHz, CDCl₃) δ 10.08 (s, 1H), 8.32-8.36 (m, 1H), 8.10-8.16 (m, 1H), 8.12 (d, J = 8.50 Hz, 1H), 7.99 (d, J = 8.50 Hz, 1H), 7.94 (d, J = 8.50 Hz, 1H), 7.78-7.85 (m, 0H), 7.48-7.59 (m, 2H), 4.90 (dd, J = 7.18, 8.35 Hz, 1H), 2.08-2.36 (m, 2H), 1.06 (t, J = 7.33 Hz, 3H) |
| 59 | 4-(5-{[1-(3-nitrophenyl)ethyl]thio}-1,3,4-oxadiazol-2-yl)benzaldehyde | 38 | ¹H NMR (300 MHz, CD₃OD) δ 8.39 (s, 1H), 8.15 (d, J = 8.20 Hz, 1H), 8.03 (d, J = 8.20 Hz, 2H), 7.96 (d, J = 7.91 Hz, 1H), 7.67 (d, J = 8.20 Hz, 2H), 7.61 (t, J = 7.62 Hz, 1H), 5.19 (q, J = 7.33 Hz, 1H), 4.29 (s, 2H), 3.20 (t, J = 7.33 Hz, 2H), 2.03 (spt, J = 7.60 Hz, 2H), 1.89 (d, J = 7.33 Hz, 6H), 1.80 (dd, J = 7.03, 7.91 Hz, 2H) |
| 60 | 4-(5-{[1-(3-chloro-2-fluorophenyl)pentyl]thio}-1,3,4-oxadiazol-2-yl)benzaldehyde | 39 | ¹H NMR (300 MHz, CDCl₃) δ 10.08 (s, 1H), 8.12 (d, J = 8.20 Hz, 1H), 8.00 (d, J = 8.79 Hz, 2H), 7.40 (ddd, J = 1.61, 6.37, 7.84 Hz, 1H), 7.32 (ddd, J = 1.61, 6.89, 8.20 Hz, 1H), 7.08 (td, J = 0.88, 7.91 Hz, 1H), 5.13 (dd, J = 6.89, 8.64 Hz, 1H), 2.03-2.29 (m, 2H), 1.26-1.50 (m, 4H), 0.90 (t, J = 7.00 Hz, 3H) |
| 61 | 4-(5-{[1-(3-chloro-2-fluorophenyl)hexyl]thio}-1,3,4-oxadiazol-2-yl)benzaldehyde | 40 | ¹H NMR (300 MHz, CDCl₃) δ 10.08 (s, 1H), 8.12 (d, J = 8.4 Hz, 1H), 8.00 (d, J = 8.7 Hz, 2H), 7.42 (ddd, J = 1.5, 6.6, 8.1 Hz, 1H), 7.32 (ddd, J = 1.5, 6.3, 7.8 Hz, 1H), 7.07 (td, J = 1.2, 7.8 Hz, 1H), 5.13 (dd, J = 6.9, 8.7 Hz, 1H), 2.04-2.23 (m, 2H), 1.25-1.56 (m, 6H), 0.87 (t, J = 7.00 Hz, 3H) |

TABLE 6-continued

| Interm. No. | Structure IUPAC name | Interm. No. | ¹H NMR δ (ppm) |
|---|---|---|---|
| 62 | 4-(5-{[1-(3-nitrophenyl)butyl]thio}-1,3,4-oxadiazol-2-yl)benzaldehyde | 41 | ¹H NMR (300 MHz, CDCl₃) δ 10.07 (s, 1H), 8.34 (t, J = 1.90 Hz, 1H), 8.10-8.15 (m, 1H), 8.12 (d, J = 8.20 Hz, 2H), 7.99 (d, J = 8.50 Hz, 2H), 7.83 (d, J = 7.62 Hz, 1H), 7.52 (t, J = 7.91 Hz, 1H), 4.98 (dd, J = 7.18, 8.35 Hz, 1H), 2.01-2.26 (m, 2H), 1.32-1.57 (m, 2H), 0.98 (t, J = 7.33 Hz, 3H) |
| 63 | 4-(5-((1-(3-chloro-2-fluorophenyl)heptyl)thio)-1,3,4-oxadiazol-2-yl)benzaldehyde | 43 | ¹H NMR (600 MHz, CDCl₃) δ: 10.09 (s, 1H), 8.13 (d, J = 8.4 Hz, 2H), 7.97-8.03 (m, 2H), 7.40 (s, 1H), 7.33 (s, 1H), 7.04-7.11 (m, 1H), 5.13 (dd, J = 8.7, 6.9 Hz, 1H), 2.17-2.26 (m, 1H), 2.06-2.14 (m, 1H), 1.42-1.52 (m, 1H), 1.20-1.40 (m, 7H), 0.87 (t, J = 7.0 Hz, 3H) |
| 64 | 4-methyl-5-(5-{[1-(3-nitrophenyl)ethyl]thio}-1,3,4-oxadiazol-2-yl)-2-furaldehyde | 44 | NMR 300 MHz (CDCL₃), δ 9.8 (s, 1H), 8.4 (m, 1H), 8.2 (m, 1H), 7.9 (d, 1H), 7.6 (t, 1H), 7.2 (s, 1H), 5.2 (q j = 6 Hz, 1H), 5.0 (q j = 6 Hz, 1H), 2.5 (s, 3H), 1.9 (d j = 6 Hz, 3H). |
| 65 | 3-Methyl-4-(5-{[1-(3-nitrophenyl)propyl]thio}-1,3,4-oxadiazol-2-yl)benzaldehyde | 45 | NMR 300 MHz (CDCl₃), δ, 10.0 (s, 1H), 8.4 (s, 1H), 8.2 (d, 1H), 8.0 (d, 1H), 7.8 (t, 3H), 7.6 (t, 1H), 4.9 (t, 1H), 2.75 (s, 3H), 2.3 (m, 1H), 2.2 (m, 1H), 1.0 (t, 3H). |
| 66 | 3-Ethyl-4-(5-{[1-(3-nitrophenyl)ethyl]thio}-1,3,4-oxadiazol-2-yl)benzaldehyde | 46 | NMR 300 MHz (CDCl₃), δ, 10.1 (s, 1H), 8.4 (s, 1H), 8.2 (d, 1H), 8.0 (d, 1H), 7.6-7.8 (m, 3H), 7.6 (t, 1H), 5.2 (q, 1H), 3.2 (q, 2H), 1.8 (d, 3H), 1.5 (t, 3H). |

TABLE 6-continued

| Interm. No. | Structure IUPAC name | Interm. No. | ¹H NMR δ (ppm) |
|---|---|---|---|
| 67 | 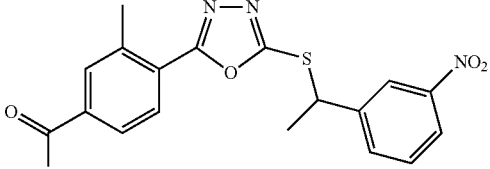<br>3-Methyl-4-(5-{[1-(3-nitrophenyl)ethyl]thio}-1,3,4-oxadiazol-2-yl)benzaldehyde | 47 | NMR 300 MHz (CDCl₃), δ, 10.0 (s, 1H), 8.4 (s, 1H), 8.2 (d, 1H), 8.0 (d, 1H), 7.8 (m, 3H), 7.6 (t, 1H), 5.2 (q, 1H), 2.75 (s, 3H), 1.9 (d, 3H). |
| 68 | 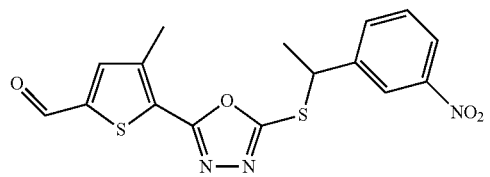 [SMILES: Cc1cc(C=O)sc1-c1nnc(SC(C)c2cccc([N+](=O)[O-])c2)o1]<br>4-Methyl-5-(5-{[1-(3-nitrophenyl)ethyl]thio}-1,3,4-oxadiazol-2-yl)thiophene-2-carboxaldehyde | 48 | NMR (300 MHz, CDCl₃) δ10 (s, 1H), 8.4 (s,1H), 8.2 (d, 1H), 7.9 (d, 1H), 7.6 (s, 1H), 7.5 (t, 1H), 5.1 (q, 1H) 2.6 (s, 3H), 1.9 (d, 3H). |
| 69 | 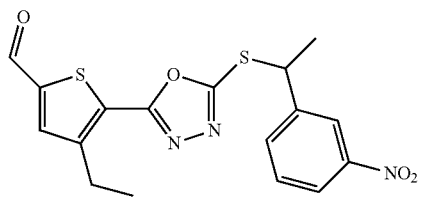 [SMILES: CCc1cc(C=O)sc1-c1nnc(SC(C)c2cccc([N+](=O)[O-])c2)o1]<br>4-Ethyl-5-(5-{[1-(3-nitrophenyl)ethyl]thio}-1,3,4-oxadiazol-2-yl)thiophene-2-carbaldehyde | 49 | NMR (300 MHz, CDCl₃) δ 10 (s, 1H), 8.4 (s, 1H), 8.2 (d, 1H), 7.8 (d, 1H), 7.7 (s, 1H), 7.6 (t, 1H), 5.2 (q, 1H), 3.1 (q, 2H), 1.9 (d, 3 H), 1.3 (t, 3H). |
| 70 | 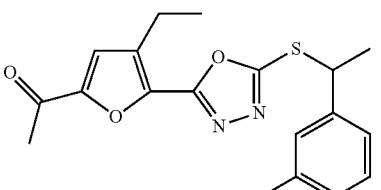<br>4-Ethyl-5-(5-{[1-(3-nitrophenyl)ethyl]thio}-1,3,4-oxadiazol-2-yl)-2-furaldehyde | 50 | NMR 300 MHz (CDCl₃), δ 9.8 (s, 1H), 8.4 (s, 1H), 8.2 (m, 1H), 7.9 (m, 1H), 7.6 (t j = 8 Hz, 1H), 7.3 (s, 1H), 5.2 (q j = 6 Hz, 1H), 5.0 (q j = 6 Hz, 1H), 2.9 (q j = 8 Hz, 2H), 1.9 (d j = 6 Hz, 3H), 1.3 (t j = 8 Hz, 3H). |

Example 9

Intermediate 71

4-(5-{[1-(3-bromophenyl)butyl]thio}-1,3,4-oxadiazol-2-yl)benzaldehyde

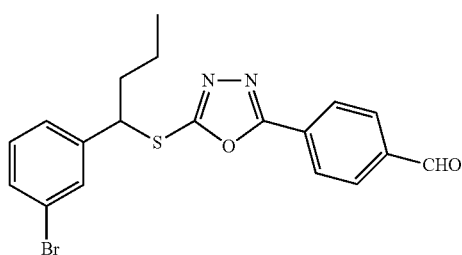 [SMILES: CCCC(Sc1nnc(-c2ccc(C=O)cc2)o1)c1cccc(Br)c1]

To a solution of Intermediate 42 (191 mg, 0.41 mmol) in acetonitrile (5 mL) was added Amberlyst 15 hydrogen foam (160 mg) and stirred at RT for 2 h. The reaction mixture was filtered and concentrated to yield 160 mg 4-(5-{[1-(3-bromophenyl)butyl]thio}-1,3,4-oxadiazol-2-yl)benzaldehyde as a yellow solid.

¹H NMR (300 MHz, CDCl₃) δ 10.08 (s, 1H), 8.12 (d, J=8.20 Hz, 2H), 7.99 (d, J=8.50 Hz, 2H), 7.59 (t, J=1.61 Hz, 1H), 7.36-7.42 (m, 2H), 7.20 (t, J=8.20 Hz, 1H), 4.82 (dd, J=6.74, 8.79 Hz, 1H), 1.96-2.21 (m, 2H), 1.32-1.52 (m, 2H), 0.96 (t, J=7.33 Hz, 3H).

Example 10

Compound 1

{3-[(4-{5-[(3-chloro-2-fluorobenzyl)thio]-1,3,4-oxadiazol-2-yl}benzyl)amino]propyl}phosphonic acid

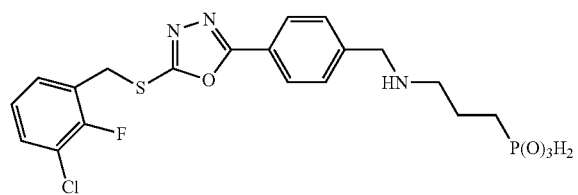

To a solution of Intermediate 51 (68 mg, 0.19 mmol) and (3-aminopropyl) phosphonic acid (27 mg) in methanol (5 mL) was added tetrabutylammonium hydroxide (1M in MeOH, 0.2 mL). The reaction mixture was heated to 50° C. for 1 h with stirring, cooled to RT, then sodium borohydride (11 mg, 0.29 mmol) was added. After the reaction mixture was stirred at RT for 3 h, the mixture was concentrated and purified by MPLC (100% methanol in ethyl acetate) to give 64 mg of {3-[(4-{5-[(3-chloro-2-fluorobenzyl)thio]-1,3,4-oxadiazol-2-yl}benzyl)amino]propyl}phosphonic acid as a colorless solid.

$^1$H NMR (300 MHz, CD$_3$OD) δ 8.08 (d, J=8.50 Hz, 2H), 7.69 (d, J=8.20 Hz, 2H), 7.51 (ddd, J=1.47, 6.74, 8.50 Hz, 1H), 7.43 (ddd, J=1.76, 7.03, 7.60 Hz, 1H), 7.14 (td, J=1.17, 7.91 Hz, 1H), 4.61 (s, 2H), 4.30 (s, 2H), 3.21 (t, J=7.47 Hz, 2H), 2.04 (tt, J=7.58, 15.13 Hz, 2H), 1.83 (dt, J=7.60, 18.46 Hz, 2H).

Compounds 2 through 21 were prepared from the corresponding starting materials, in a similar manner to the procedure described in Example 10 for Compound 1. The results are tabulated below in Table 7.

TABLE 7

| Cmpd No. | Structure<br>IUPAC name | Interm. No. | $^1$H NMR δ (ppm) |
|---|---|---|---|
| 2 | 3-[(4-{5-[(3-chloro-2-fluorobenzyl)thio]-1,3,4-oxadiazol-2-yl}benzyl)amino]propanoic acid | 51 | $^1$H NMR (300 MHz, CD$_3$OD) δ 8.02 (d, J = 8.20 Hz, 2H), 7.65 (d, (d, J = 8.20 Hz, 2H), 7.50 (ddd, J = 1.76, 6.15, 8.20 Hz, 1H), 7.42 (ddd, J = 1.47, 6.74, 8.20 Hz, 1H), 7.13 (td, J = 1.17, 7.91 Hz, 1H), 4.60 (s, 2H), 4.16 (br. s., 2H), 3.04-3.12 (m, 2H), 2.49 (t, J = 6.45 Hz, 2H) |
| 3 | 2-[(4-{5-[(3-chloro-2-fluorobenzyl)thio]-1,3,4-oxadiazol-2-yl}benzyl)amino]ethyl dihydrogen phosphate | 51 | $^1$H NMR (300 MHz, CD$_3$OD) δ 8.08 (d, J = 8.50 Hz, 2H), 7.71 (d, J = 8.50 Hz, 2H), 7.51 (ddd, J = 1.76, 6.45, 7.62 Hz, 1H), 7.42 (ddd, J = 1.76, 6.74, 8.20 Hz, 1H), 7.13 (ddd, J = 1.17, 7.62, 8.20 Hz, 1H), 4.56-4.69 (m, 2H), 4.37 (s, 2H), 4.26-4.33 (m, 2H), 3.40 (t, J = 4.70 Hz, 2H) |
| 4 | 2-[(4-{5-[(3-chloro-2-fluorobenzyl)thio]-1,3,4-oxadiazol-2-yl}benzyl)amino]ethanol | 51 | $^1$H NMR (300 MHz, CD$_3$OD) δ 7.96 (d, J = 8.50 Hz, 2H), 7.56 (d, J = 8.20 Hz, 2H), 7.50 (ddd, J = 1.17, 6.74, 7.91 Hz, 1H), 7.42 (ddd, J = 1.76, 7.03, 8.50 Hz, 1H), 7.13 (ddd, J = 1.17, 7.62, 8.20 Hz, 1H), 4.59 (s, 2H), 3.89 (s, 2H), 3.68 (t, J = 5.57 Hz, 2H), 2.75 (t, J = 5.42 Hz, 2H) |

TABLE 7-continued

| Cmpd No. | Structure IUPAC name | Interm. No. | $^1$H NMR δ (ppm) |
|---|---|---|---|
| 5 | 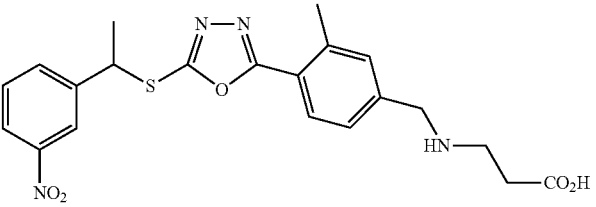 [SMILES: Cc1cc(CNCCC(=O)O)ccc1-c1nnc(SC(C)c2cccc([N+](=O)[O-])c2)o1]<br>3-{[3-methyl-4-(5-{[1-(3-nitrophenyl)ethyl]thio}-1,3,4-oxadiazol-2-yl)benzyl]amino}propanoic acid | 67 | $^1$H NMR (300 MHz, CD$_3$OD) δ 8.37 (t, J = 2.05 Hz, 1H), 8.14 (ddd, J = 1.03, 2.20, 8.20 Hz, 1H), 7.92-7.96 (m, 1H), 7.83 (d, J = 8.20 Hz, 1H), 7.60 (t, J = 8.06 Hz, 1H), 7.49 (s, 1H), 7.45 (dd, J = 1.76, 8.20 Hz, 1H), 5.48 (s, 1H), 5.17 (q, J = 7.03 Hz, 1H), 4.19 (s, 2H), 3.15 (t, J = 6.45 Hz, 2H), 2.60 (s, 3H), 2.50 (t, J = 6.45 Hz, 2H), 1.88 (d, J = 7.33 Hz, 3H) |
| 6 | 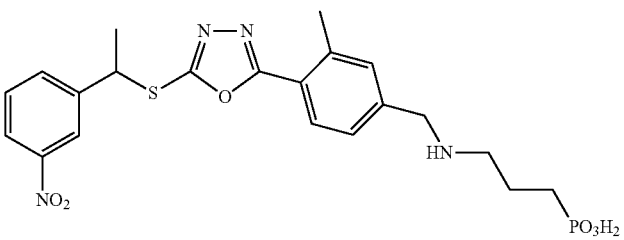<br>(3-{[3-methyl-4-(5-{[1-(3-nitrophenyl)ethyl]thio}-1,3,4-oxadiazol-2-yl)benzyl]amino}propyl)phosphonic acid | 67 | $^1$H NMR (300 MHz, CD$_3$OD) δ8.38 (t, J = 2.05 Hz, 1H), 8.15 (ddd, J = 1.03, 2.20, 8.20 Hz, 1H), 7.96 (dt, J = 1.17, 7.91 Hz, 1H), 7.88 (d, J = 7.91 Hz, 1H), 7.61 (t, J = 8.06 Hz, 1H), 7.51 (s, 1H), 7.47 (dd, J = 1.61, 8.06 Hz, 1H), 5.18 (q, J = 7.03 Hz, 1H), 4.25 (s, 2H), 3.19 (t, J = 7.33 Hz, 2H), 2.63 (s, 3H), 2.03 (tt, J = 7.36, 14.91 Hz, 2H), 1.89 (d, J = 7.33 Hz, 3H), 1.77-1.89 (m, 2H) |
| 7 | 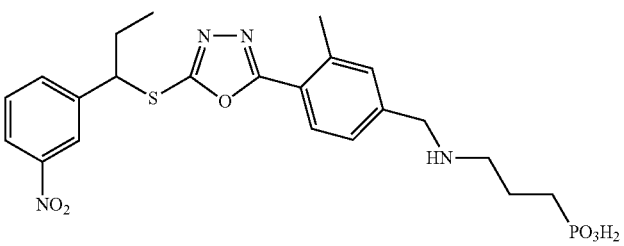<br>(3-{[3-methyl-4-(5-{[1-(3-nitrophenyl)propyl]thio}-1,3,4-oxadiazol-2-yl)benzyl]amino}propyl)phosphonic acid | 66 | $^1$H NMR (300 MHz, CD$_3$OD) δ8.34 (s, 1H), 8.15 (dd, J = 1.61, 8.06 Hz, 1H), 7.91 (d, J = 7.91 Hz, 1H), 7.87 (d, J = 8.20 Hz, 1H), 7.61 (t, J = 7.91 Hz, 1H), 7.51 (s, 1H), 7.46 (d, J = 8.50 Hz, 1H), 4.92 (t, J = 7.76 Hz, 1H), 4.24 (s, 2H), 3.19 (t, J = 7.62 Hz, 2H), 2.62 (s, 3H), 2.19-2.34 (m, J = 7.18, 7.18, 7.33, 14.36 Hz, 1H), 2.17 (dd, J = 7.18, 14.80 Hz, 1H), 2.03 (dquin, J = 7.50, 15.16 Hz, 2H), 1.77-1.90 (m, 2H) |
| 8 | 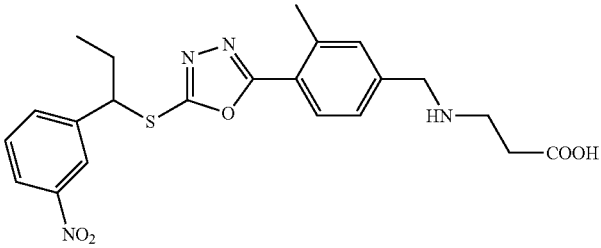 [SMILES: CCC(Sc1nnc(-c2ccc(CNCCC(=O)O)cc2C)o1)c1cccc([N+](=O)[O-])c1]<br>3-{[3-methyl-4-(5-{[1-(3-nitrophenyl)propyl]thio}-1,3,4-oxadiazol-2-yl)benzyl]amino}propanoic acid | 66 | $^1$H NMR (300 MHz, CD$_3$OD) δ8.34 (s, 1H), 8.14 (d, J = 8.20 Hz, 1H), 7.90 (d, J = 7.91 Hz, 1H), 7.84 (d, J = 7.91 Hz, 1H), 7.60 (t, J = 8.20 Hz, 1H), 7.49 (s, 1H), 7.45 (d, J = 8.50 Hz, 1H), 4.92 (t, J = 7.62 Hz, 1H), 4.19 (s, 2H), 3.15 (t, J = 6.30 Hz, 2H), 2.60 (s, 3H), 2.50 (t, J = 6.30 Hz, 2H), 2.25 (spt, J = 7.00 Hz, 1H), 2.14 (q, J = 7.30 Hz, 1H), 1.05 (t, J = 7.33 Hz, 3H) |

TABLE 7-continued

| Cmpd No. | Structure / IUPAC name | Interm. No. | $^1$H NMR δ (ppm) |
|---|---|---|---|
| 9 | 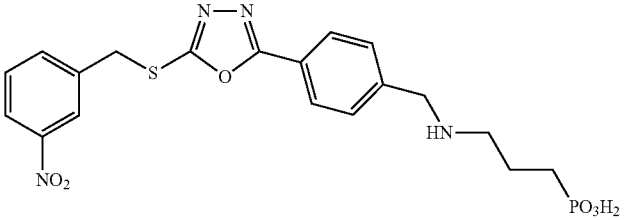<br>{3-[(4-{5-[(3-nitrobenzyl)thio]-1,3,4-oxadiazol-2-yl}benzyl)amino]propyl}phosphonic acid | 52 | $^1$H NMR (300 MHz, CD$_3$OD) δ8.43 (t, J = 2.05 Hz, 1H), 8.17 (ddd, J = 1.03, 2.34, 8.35 Hz, 1H), 8.08 (d, J = 8.50 Hz, 2H), 7.93 (ddd, J = 0.88, 1.76, 7.62 Hz, 1H), 7.68 (d, J = 8.50 Hz, 2H), 7.60 (t, J = 8.06 Hz, 1H), 4.67 (s, 2H), 4.29 (s, 2H), 3.20 (t, J = 7.62 Hz, 2H), 1.96-2.12 (m, 2H), 1.88 (d, J = 7.91 Hz, 1H), 1.81 (dd, J = 7.03, 7.62 Hz, 1H) |
| 10 | 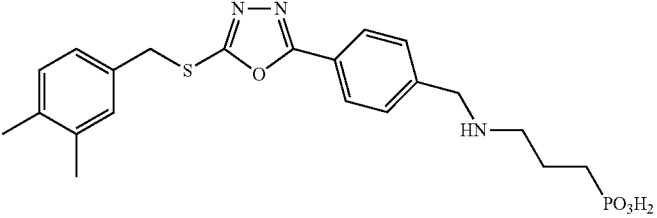<br>{3-[(4-{5-[(3,4-dimethylbenzyl)thio]-1,3,4-oxadiazol-2-yl}benzyl)amino]propyl}phosphonic acid | 53 | $^1$H NMR (300 MHz, CD$_3$OD) δ8.08 (d, J = 8.50 Hz, 2H), 7.69 (d, J = 8.50 Hz, 2H), 7.22 (s, 1H), 7.17 (dd, J = 2.05, 7.62 Hz, 1H), 7.08 (d, J = 7.91 Hz, 1H), 4.49 (s, 2H), 4.30 (s, 2H), 3.21 (t, J = 7.33 Hz, 2H), 2.23 (s, 3H), 2.23 (s, 3H), 1.97-2.12 (m, 2H), 1.88 (d, J = 7.33 Hz, 1H), 1.81 (dd, J = 7.03, 7.91 Hz, 1H) |
| 11 | 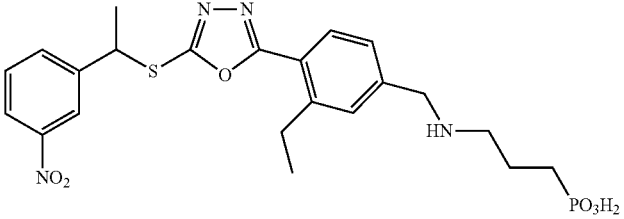<br>(3-{[3-ethyl-4-(5-{[1-(3-nitrophenyl)ethyl]thio}-1,3,4-oxadiazol-2-yl)benzyl]amino}propyl)phosphonic acid | 66 | $^1$H NMR (300 MHz, CD$_3$OD) δ 8.37 (t, J = 1.90 Hz, 1H), 8.15 (ddd, J = 1.03, 2.20, 8.20 Hz, 1H), 7.95 (d, J = 7.91 Hz, 1H), 7.85 (d, J = 7.91 Hz, 1H), 7.61 (t, J = 7.91 Hz, 1H), 7.54 (d, J = 1.47 Hz, 1H), 7.47 (dd, J = 1.76, 8.20 Hz, 1H), 5.17 (q, J = 7.03 Hz, 1H), 4.26 (s, 2H), 3.20 (t, J = 7.33 Hz, 2H), 3.03 (q, J = 7.33 Hz, 2H), 2.04 (ddq, J = 7.59, 7.76, 15.16 Hz, 2H), 1.89 (d, J = 7.03 Hz, 3H), 1.81 (dd, J = 7.33, 7.91 Hz, 1H), 1.21 (t, J = 7.47 Hz, 3H) |
| 12 | 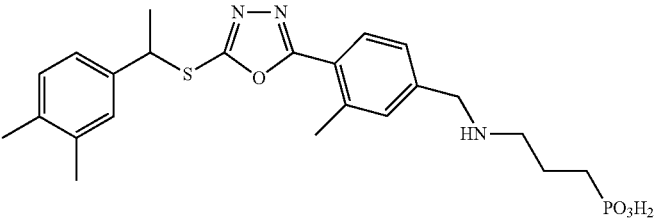<br>(3-{[4-(5-{[1-(3,4-dimethylphenyl)ethyl]thio}-1,3,4-oxadiazol-2-yl)benzyl]amino}propyl)phosphonic acid | | $^1$H NMR (300 MHz, CD$_3$OD) δ 8.04 (d, J = 8.20 Hz, 2H), 7.68 (d, J = 8.50 Hz, 2H), 7.22 (s, 1H), 7.17 (dd, J = 1.76, 7.91 Hz, 1H), 7.08 (d, J = 7.91 Hz, 1H), 4.97 (q, J = 7.00 Hz, 1H), 4.30 (s, 2H), 3.21 (t, J = 7.62 Hz, 2H), 2.23 (s, 3H), 2.21 (s, 3H), 2.04 (spt, J = 7.60 Hz, 2H), 1.82 (d, J = 8.20 Hz, 3H), 1.77-1.89 (m, 2H) |

TABLE 7-continued

| Cmpd No. | Structure IUPAC name | Interm. No. | ¹H NMR δ (ppm) |
|---|---|---|---|
| 13 | 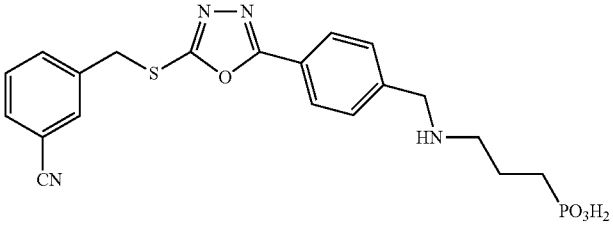<br>{3-[(4-{5-[(3-cyanobenzyl)thio]-1,3,4-oxadiazol-2-yl}benzyl)amino]propyl}phosphonic acid | 55 | ¹H NMR (300 MHz, CD₃OD) δ 8.07 (d, J = 8.50 Hz, 2H), 7.90 (s, 1H), 7.84 (d, J = 7.91 Hz, 1H), 7.63-7.71 (m, 3H), 7.53 (t, J = 7.62 Hz, 1H), 4.60 (s, 2H), 4.30 (s, 2H), 3.20 (t, J = 7.76 Hz, 2H), 2.03 (dquin, J = 7.60, 15.02 Hz, 2H), 1.77-1.89 (m, 2H) |
| 14 | 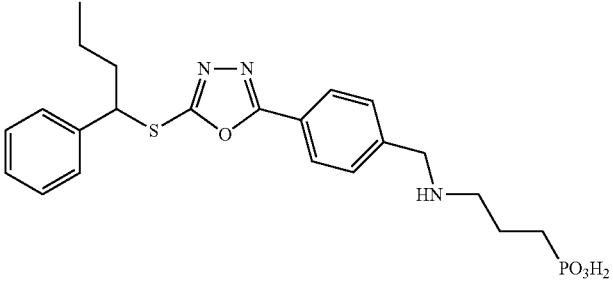<br>{3-[(4-{5-[(1-phenylbutyl)thio]-1,3,4-oxadiazol-2-yl}benzyl)amino]propyl}phosphonic acid | 56 | ¹H NMR (300 MHz, CD₃OD) δ 8.02 (d, J = 8.50 Hz, 2H), 7.67 (d, J = 8.20 Hz, 2H), 7.44 (d, J = 7.03 Hz, 2H), 7.25-7.35 (m, 3H), 4.86 (dd, J = 6.74, 9.08 Hz, 1H), 4.29 (s, 2H), 3.20 (t, J = 7.76 Hz, 2H), 1.95-2.21 (m, 4H), 1.77-1.90 (m, 2H), 1.30-1.48 (m, 2H), 0.96 (t, J = 7.60 Hz, 3H) |
| 15 | 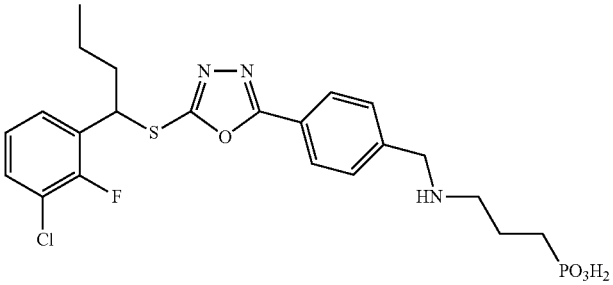<br>(3-{[4-(5-{[1-(3-chloro-2-fluorophenyl)butyl]thio}-1,3,4-oxadiazol-2-yl)benzyl]amino}propyl)phosphonic acid | 57 | ¹H NMR (300 MHz, CD₃OD) δ 8.03 (d, J = 8.20 Hz, 2H), 7.68 (d, J = 8.20 Hz, 2H), 7.50 (ddd, J = 1.47, 6.74, 8.20 Hz, 1H), 7.40 (ddd, J = 1.47, 6.74, 8.20 Hz, 1H), 7.16 (t, J = 7.91 Hz, 1H), 5.14-5.20 (m, 1H), 4.30 (s, 2H), 3.20 (t, J = 7.47 Hz, 2H), 1.96-2.23 (m, 4H), 1.77-1.90 (m, 2H), 1.32-1.54 (m, 2H), 0.98 (t, J = 7.33 Hz, 3H) |
| 16 | 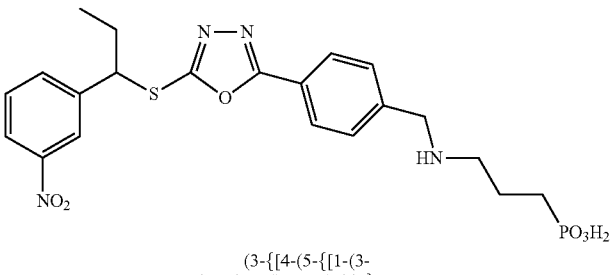<br>(3-{[4-(5-{[1-(3-nitrophenyl)propyl]thio}-1,3,4-oxadiazol-2-yl)benzyl]amino}propyl)phosphonic acid | 58 | ¹H NMR (300 MHz, CD₃OD) δ 8.36 (s, 1H), 8.14 (dd, J = 1.61, 7.76 Hz, 1H), 8.02 (d, J = 8.20 Hz, 2H), 7.91 (d, J = 7.91 Hz, 1H), 7.66 (d, J = 8.50 Hz, 2H), 7.60 (dd, J = 7.03, 7.91 Hz, 1H), 4.93 (t, J = 7.62 Hz, 1H), 4.29 (s, 2H), 3.20 (t, J = 7.76 Hz, 2H), 2.14-2.33 (m, 2H), 1.96-2.12 (m, 2H), 1.78-1.91 (m, 2H), 1.06 (t, J = 7.33 Hz, 3H) |

TABLE 7-continued

| Cmpd No. | Structure IUPAC name | Interm. No. | $^1$H NMR δ (ppm) |
|---|---|---|---|
| 17 | 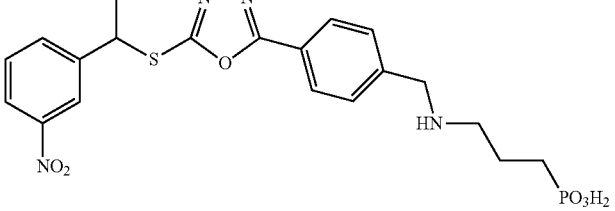<br>(3-{[4-(5-{[1-(3-nitrophenyl)ethyl]thio}-1,3,4-oxadiazol-2-yl)benzyl]amino}propyl)phosphonic acid | 59 | $^1$H NMR (300 MHz, CD$_3$OD) δ 8.39 (s, 1H), 8.15 (d, J = 8.20 Hz, 1H), 8.03 (d, J = 8.20 Hz, 2H), 7.96 (d, J = 7.91 Hz, 1H), 7.67 (d, J = 8.20 Hz, 2H), 7.61 (t, J = 7.62 Hz, 1H), 5.19 (q, J = 7.33 Hz, 1H), 4.29 (s, 2H), 3.20 (t, J = 7.33 Hz, 2H), 2.03 (spt, J = 7.60 Hz, 2H), 1.89 (d, J = 7.33 Hz, 6H), 1.80 (dd, J = 7.03, 7.91 Hz, 2H) |
| 18 | 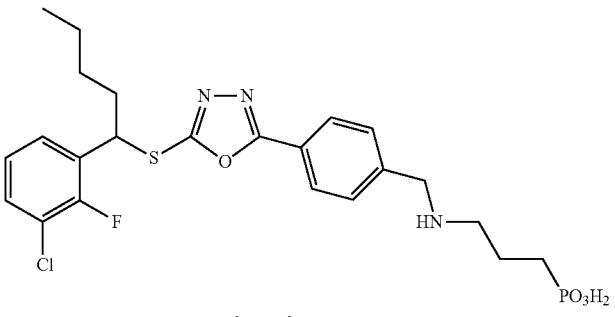<br>(3-{[4-(5-{[1-(3-chloro-2-fluorophenyl)pentyl]thio}-1,3,4-oxadiazol-2-yl)benzyl]amino}propyl)phosphonic acid | 60 | $^1$H NMR (300 MHz, CD$_3$OD) δ 8.03 (d, J = 8.20 Hz, 2H), 7.68 (d, J = 8.20 Hz, 2H), 7.49 (ddd, J = 1.47, 6.45, 7.91 Hz, 1H), 7.40 (ddd, J = 1.47, 6.74, 8.20 Hz, 1H), 7.16 (ddd, J = 0.88, 7.62, 8.20 Hz, 1H), 5.15 (dd, J = 7.03, 8.50 Hz, 1H), 4.30 (s, 2H), 3.20 (t, J = 7.62 Hz, 2H), 1.96-2.25 (m, 4H), 1.77-1.90 (m, 2H), 1.27-1.51 (m, 4H), 0.91 (t, J = 7.03 Hz, 3H) |
| 19 | 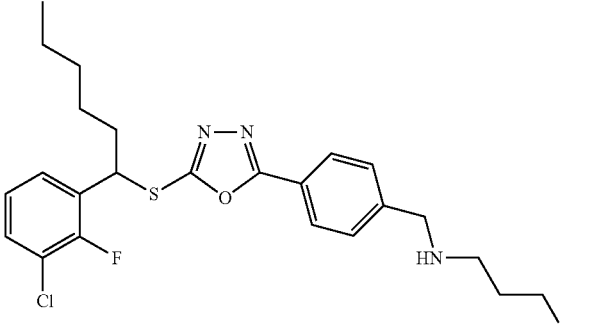<br>(3-{[4-(5-{[1-(3-chloro-2-fluorophenyl)hexyl]thio}-1,3,4-oxadiazol-2-yl)benzyl]amino}propyl)phosphonic acid | 63 | $^1$H NMR (300 MHz, CD$_3$OD) δ 8.03 (d, J = 8.20 Hz, 2H), 7.68 (d, J = 8.20 Hz, 2H), 7.50 (ddd, J = 0.88, 6.45, 7.20 Hz, 1H), 7.40 (ddd, J = 1.47, 6.40, 8.20 Hz, 1H), 7.17 (t, J = 7.91 Hz, 1H), 5.15 (dd, J = 6.89, 8.35 Hz, 1H), 4.30 (s, 2H), 3.20 (dd, J = 7.03, 8.20 Hz, 2H), 1.96-2.25 (m, 4H), 1.77-1.90 (m, 2H), 1.27-1.50 (m, 6H), 0.88 (t, J = 7.33 Hz, 3H) |
| 20 | 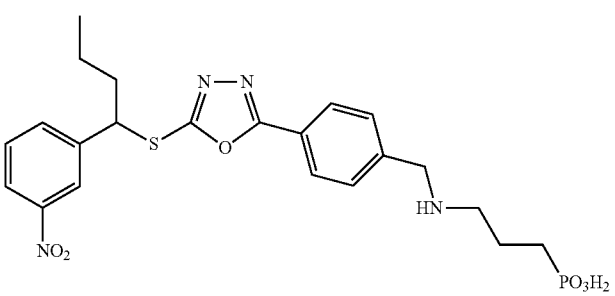<br>(3-{[4-(5-{[1-(3-nitrophenyl)butyl]thio}-1,3,4-oxadiazol-2-yl)benzyl]amino}propyl)phosphonic acid | 62 | $^1$H NMR (300 MHz, CD$_3$OD) δ 8.36 (s, 1H), 8.13 (dd, J = 1.90, 8.35 Hz, 1H), 8.02 (d, J = 8.50 Hz, 2H), 7.92 (d, J = 7.91 Hz, 1H), 7.66 (d, J = 8.20 Hz, 2H), 7.60 (dd, J = 7.62, 8.20 Hz, 1H), 5.02 (t, J = 7.60 Hz, 1H), 4.29 (s, 2H), 3.19 (t, J = 7.47 Hz, 2H), 1.96-2.27 (m, 4H), 1.75-1.91 (m, 2H), 1.33-1.58 (m, 2H), 0.99 (t, J = 7.90 Hz, 3H) |

| Cmpd No. | Structure IUPAC name | Interm. No. | $^1$H NMR δ (ppm) |
|---|---|---|---|
| 21 | (3-{[4-(5-{[1-(3-bromophenyl)butyl]thio}-1,3,4-oxadiazol-2-yl)benzyl]amino}propyl)phosphonic acid | 71 | $^1$H NMR (300 MHz, CD$_3$OD) δ 8.03 (d, J = 8.7 Hz, 2H), 7.68 (d, J = 8.1 Hz, 2H), 7.64 (s, 1H), 7.43 (dd, J = 7.5, 9.0 Hz, 1H), 4.83 (dd, J = 6.74, 8.79 Hz, 1H), 4.29 (s, 2H), 3.20 (dd, J = 7.5, 8.4 Hz, 2H), 1.88-2.21 (m, 4H), 1.77-1.86 (m, 2H), 1.35-1.48 (m, 2H), 0.99 (t, J = 7.90 Hz, 3H) |
| 22 | (3-((4-(5-((1-(3-chloro-2-fluorophenyl)heptyl)thio)-1,3,4-oxadiazol-2-yl)benzyl)amino)propyl)phosphonic acid | 63 | $^1$H NMR ((600 MHz, CD$_3$OD) δ: 7.86 (d, J = 8.4 Hz, 2H), 7.51 (d, J = 8.5 Hz, 2H), 7.30-7.34 (m, 1H), 7.20-7.25 (m, 1H), 6.98-7.02 (m, 1H), 4.96-5.00 (m, 1H), 4.12 (s, 2H), 3.02 (d, J = 7.8 Hz, 2H), 2.00-2.08 (m, 1H), 1.92-1.98 (m, 1H), 1.82-1.90 (m, 2H), 1.62-1.70 (m, 2H), 1.07-1.33 (m, 8H), 0.71 (t, J = 7.0 Hz, 3H) |
| 23 | 3-[(4-{5-[(1-phenylbutyl)sulfanyl]-1,3,4-oxadiazol-2-yl}benzyl)amino]propanoic acid | 56 | $^1$H NMR (600 MHz, CD$_3$OD) δ: 7.99 (dd, J = 8.0, 2.0 Hz, 2H), 7.66 (d, J = 8.1 Hz, 2H), 7.44 (d, J = 7.8 Hz, 2H), 7.33 (t, J = 7.6 Hz, 2H), 7.23-7.58 (m, 1H), 4.83-4.91 (m, 1H), 4.26 (s, 2H), 3.18 (t, J = 6.4 Hz, 2H), 2.52 (t, J = 6.4 Hz, 2H), 2.02-2.22 (m, 2H), 1.29-1.49 (m, 2H), 0.96 (t, J = 7.3 Hz, 3H) |
| 24 | [3-({[4-methyl-5-(5-{[1-(3-nitrophenyl)ethyl]sulfanyl}-1,3,4-oxadiazol-2-yl)furan-2-yl]methyl}amino)propyl]phosphonic acid | 64 | $^1$H NMR (300 MHz, CD$_3$OD) δ: 8.05-8.09 (m, 1H), 7.83-7.89 (m, 1H), 7.61-7.67 (m, 1H), 7.27-7.35 (m, 1H), 6.44 (s, 1H), 4.87 (m, 1H), 4.05 (s, 2H), 2.85-2.93 (m, 2H), 2.03 (s, 3H), 1.63-1.80 (m, 2H), 1.59 (d, J = 7.2 Hz, 3H), 1.45-1.56 (m, 2H) |

TABLE 7-continued

| Cmpd No. | Structure IUPAC name | Interm. No. | $^1$H NMR δ (ppm) |
|---|---|---|---|
| 25 | 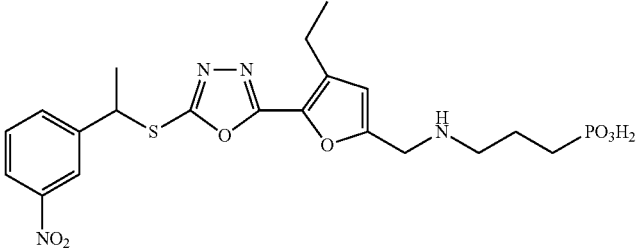 [3-({[4-ethyl-5-(5-{[1-(3-nitrophenyl)ethyl]sulfanyl}-1,3,4-oxadiazol-2-yl)furan-2-yl]methyl}amino)propyl]phosphonic acid | 70 | $^1$H NMR (300 MHz, CD$_3$OD) δ: 8.36 (s, 1H), 8.10-8.19 (m, 1H), 7.92 (d, J = 7.8 Hz, 1H), 7.53-7.65 (m, 1H), 6.76 (s, 1H), 5.13 (q, J = 7.1 Hz, 1H), 4.17 (s, 2H), 3.03 (t, J = 6.3 Hz, 2H), 2.74 (q, J = 7.6 Hz, 2H), 1.89-2.03 (m, 2H), 1.87 (d, J = 7.2 Hz, 3H), 1.58-1.75 (m, 2H), 1.20 (t, J = 7.6 Hz, 3H) |
| 26 | 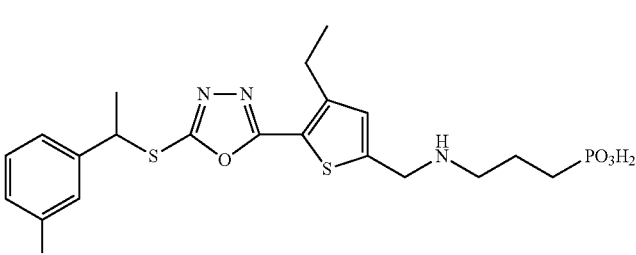 [3-({[4-ethyl-5-(5-{[1-(3-nitrophenyl)ethyl]sulfanyl}-1,3,4-oxadiazol-2-yl)thiophen-2-yl]methyl}amino)propyl]phosphonic acid | 69 | $^1$H NMR (300 MHz, CD$_3$OD) δ: 8.30-8.35 (m, 1H), 8.09-8.17 (m, 1H), 7.88-7.95 (m, 1H), 7.54-7.64 (m, 1H), 7.24-7.30 (m, 1H), 5.05-5.17 (m, 1H), 4.40-4.45 (m, 2H), 3.12-3.21 (m, 2H), 2.86-2.94 (m, 2H), 1.91-2.08 (m, 2H), 1.82-1.87 (m, 3H), 1.73-1.82 (m, 2H), 1.17-1.24 (m, 3H) |
| 27 | 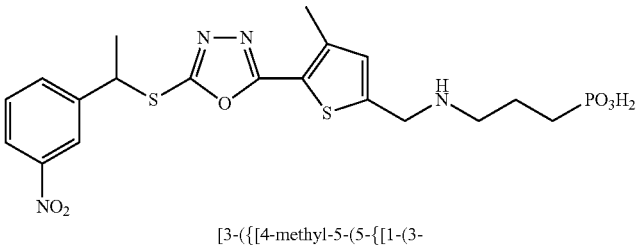 [3-({[4-methyl-5-(5-{[1-(3-nitrophenyl)ethyl]sulfanyl}-1,3,4-oxadiazol-2-yl)thiophen-2-yl]methyl}amino)propyl]phosphonic acid | 68 | $^1$H NMR (300 MHz, CD$_3$OD) δ: 8.16-8.25 (m, 1H), 7.94-8.04 (m, 1H), 7.72-7.83 (m, 1H), 7.40-7.51 (m, 1H), 7.02-7.10 (m, 1H), 4.92-5.04 (m, 1H), 4.28 (s, 2H), 2.97-3.08 (m, 2H), 2.33 (s, 3H), 1.75-1.95 (m, 2H), 1.68-1.74 (m, 3H), 1.60-1.68 (m, 2H) |

Example 11

Biological Data

Compounds were synthesized and tested for S1P1 activity using the GTP γ$^{35}$S binding assay. These compounds may be assessed for their ability to activate or block activation of the human S1P1 receptor in cells stably expressing the S1P1 receptor.

GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P1 in the presence of test antagonist at concentrations ranging from 0.08 to 5000 nM.

Table 8 shows activity potency: S1P1 receptor from GTP γ$^{35}$S: nM, (EC$_{50}$)

TABLE 8

| IUPAC Name | S1P1 EC$_{50}$ (nM) |
|---|---|
| (3-{[4-({[5-(3,4-dimethylphenyl)-1,3,4-oxadiazol-2-yl]thio}methyl)benzyl]amino}propyl)phosphonic acid | 805 |
| {3-[(4-{5-[(3-chloro-2-fluorobenzyl)thio]-1,3,4-oxadiazol-2-yl}benzyl)amino]propyl}phosphonic acid | 853 |

TABLE 8-continued

| IUPAC Name | S1P1 EC$_{50}$ (nM) |
|---|---|
| (3-{[3-methyl-4-(5-{[1-(3-nitrophenyl)ethyl]thio}-1,3,4-oxadiazol-2-yl)benzyl]amino}propyl)phosphonic acid | 231 |
| (3-{[3-methyl-4-(5-{[1-(3-nitrophenyl)propyl]thio}-1,3,4-oxadiazol-2-yl)benzyl]amino}propyl)phosphonic acid | 50 |
| (3-{[4-(1-{[5-(3,4-dimethylphenyl)-1,3,4-oxadiazol-2-yl]thio}ethyl)benzyl]amino}propyl)phosphonic acid | 888 |
| {3-[(4-{5-[(3-nitrobenzyl)thio]-1,3,4-oxadiazol-2-yl}benzyl)amino]propyl}phosphonic acid | 1815 |
| {3-[(4-{5-[(3,4-dimethylbenzyl)thio]-1,3,4-oxadiazol-2-yl}benzyl)amino]propyl}phosphonic acid | 97 |
| (3-{[3-ethyl-4-(5-{[1-(3-nitrophenyl)ethyl]thio}-1,3,4-oxadiazol-2-yl)benzyl]amino}propyl)phosphonic acid | 30 |
| (3-{[4-(5-{[1-(3,4-dimethylphenyl)ethyl]thio}-1,3,4-oxadiazol-2-yl)benzyl]amino}propyl)phosphonic acid | 1053 |
| [3-({[4-ethyl-5-(5-{[1-(3-nitrophenyl)ethyl]thio}-1,3,4-oxadiazol-2-yl)-2-thienyl]methyl}amino)propyl]phosphonic acid | 1258 |
| {3-[(4-{5-[(1-phenylbutyl)thio]-1,3,4-oxadiazol-2-yl}benzyl)amino]propyl}phosphonic acid | 1.5 |
| (3-{[4-(5-{[1-(3-chloro-2-fluorophenyl)butyl]thio}-1,3,4-oxadiazol-2-yl)benzyl]amino}propyl)phosphonic acid | 1.8 |
| (3-{[4-(5-{[1-(3-nitrophenyl)propyl]thio}-1,3,4-oxadiazol-2-yl)benzyl]amino}propyl)phosphonic acid | 40 |
| (3-{[4-(5-{[1-(3-nitrophenyl)ethyl]thio}-1,3,4-oxadiazol-2-yl)benzyl]amino}propyl)phosphonic acid | 382 |
| [3-({[4-methyl-5-(5-{[1-(3-nitrophenyl)ethyl]thio}-1,3,4-oxadiazol-2-yl)-2-thienyl]methyl}amino)propyl]phosphonic acid | 200 |

What is claimed is:

1. A compound having Formula I, its enantiomers, diastereoisomers, tautomers or a pharmaceutically acceptable salt thereof,

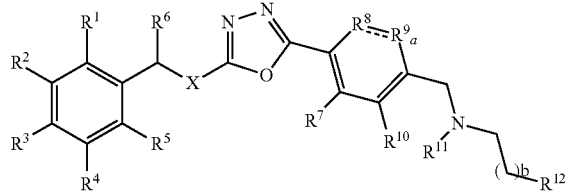

Formula I wherein:
X is S, SO or SO$_2$;
R$^1$ is hydrogen, halogen, substituted or unsubstituted C$_{1-8}$ alkyl, NO$_2$, CN, C(O)R$^{13}$ or OR$^{14}$;
R$^2$ is hydrogen, halogen, substituted or unsubstituted C$_{1-8}$ alkyl, NO$_2$, CN, C(O)R$^{13}$ or OR$^{14}$;
R$^3$ is hydrogen, halogen, substituted or unsubstituted C$_{1-8}$ alkyl, NO$_2$, CN, C(O)R$^{13}$ or OR$^{14}$;
R$^4$ is hydrogen, halogen, substituted or unsubstituted C$_{1-8}$ alkyl, NO$_2$, CN, C(O)R$^{13}$ or OR$^{14}$;
R$^5$ is hydrogen, halogen, substituted or unsubstituted C$_{1-8}$ alkyl, NO$_2$, CN, C(O)R$^{13}$ or OR$^{14}$;
R$^6$ is H, halogen, OR$^{14}$, substituted or unsubstituted C$_{1-8}$ alkyl;
R$^7$ is hydrogen, halogen, substituted or unsubstituted C$_{1-8}$ alkyl, NO$_2$, CN, C(O)R$^{13}$ or OR$^{14}$;
R$^8$ is CH, S, O, N, NH or CH$_2$;
R$^9$ is CH or CH$_2$;
R$^{10}$ is hydrogen, halogen, substituted or unsubstituted C$_{1-8}$ alkyl, C(O)R$^{13}$ or OR$^{14}$;
R$^{11}$ is H or substituted or unsubstituted C$_{1-8}$ alkyl;
R$^{12}$ is OPO$_3$H$_2$, carboxylic acid, PO$_3$H$_2$, —P(O)MeOH, —P(O)(H)OH or OR$^{14}$;
a is 0 or 1;
b is 1, 2, 3, 4, 5 or 6;
R$^{13}$ is OH or C$_{1-8}$ alkyl;
R$^{14}$ is H or C$_{1-8}$ alkyl;
when a is 1 then

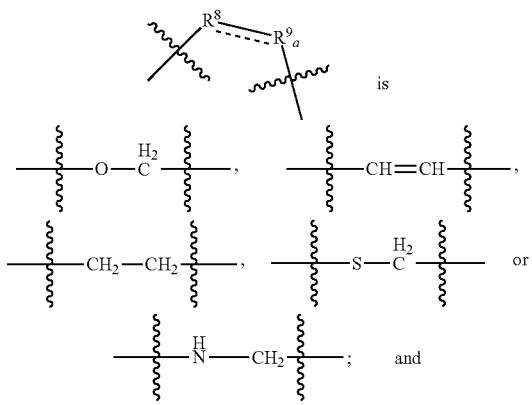

when a is 0 then

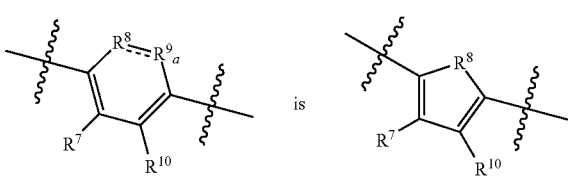

and R$^8$ is S, O, NH or CH$_2$.

2. A compound according to claim 1, wherein:
X is S.

3. A compound according to claim 1, wherein:
X is S;
a is 0;
R$^{12}$ is P(O)$_3$H$_2$; and
R$^8$ is S or O.

4. A compound according to claim 1, wherein:
X is S;
a is 1;
R$^{12}$ is carboxylic acid, PO$_3$H$_2$ or OR$^{14}$;
R$^{14}$ is H; and

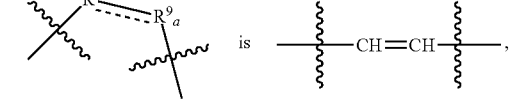

5. A compound according to claim 1 selected from:
3-[(4-{5-[(3-Chloro-2-fluorobenzyl)thio]-1,3,4-oxadiazol-2-yl}benzyl)amino]propanoic acid;
2-[(4-{5-[(3-Chloro-2-fluorobenzyl)thio]-1,3,4-oxadiazol-2-yl}benzyl)amino]ethyl dihydrogen phosphate;
2-[(4-{5-[(3-Chloro-2-fluorobenzyl)thio]-1,3,4-oxadiazol-2-yl}benzyl)amino]ethanol;
3-{[3-methyl-4-(5-{[1-(3-nitrophenyl)ethyl]thio}-1,3,4-oxadiazol-2-yl)benzyl]amino}propanoic acid;
(3-{[3-Methyl-4-(5-{[1-(3-nitrophenyl)ethyl]thio}-1,3,4-oxadiazol-2-yl)benzyl]amino}propylphosphonic acid;
(3-{[3-Methyl-4-(5-{[1-(3-nitrophenyl)propyl]thio}-1,3,4-oxadiazol-2-yl)benzyl]amino}propyl)phosphonic acid 3-{[3-Methyl-4-(5-{[1-(3-nitrophenyl)propyl]thio}-1,3,4-oxadiazol-2-yl)benzyl]amino}propanoic acid;
{3-[(4-{5-[(3-Nitrobenzyl)thio]-1,3,4-oxadiazol-2-yl}benzyl)amino]propyl}phosphonic acid;
{3-[(4-{5-[(3,4-Dimethylbenzyl)thio]-1,3,4-oxadiazol-2-yl}benzyl)amino]propyl}phosphonic acid;
(3-{[3-ethyl-4-(5-{[1-(3-Nitrophenyl)ethyl]thio}-1,3,4-oxadiazol-2-yl)benzyl]amino}propyl)phosphonic acid;
(3-{[4-(5-{[1-(3,4-Dimethylphenyl)ethyl]thio}-1,3,4-oxadiazol-2-yl)benzyl]amino}propyl)phosphonic acid;
{3-[(4-{5-[(3-Cyanobenzyl)thio]-1,3,4-oxadiazol-2-yl}benzyl)amino]propyl}phosphonic acid;
{3-[(4-{5-[(1-phenylbutyl)thio]-1,3,4-oxadiazol-2-yl}benzyl)amino]propyl}phosphonic acid;
(3-{[4-(5-{[1-(3-Chloro-2-fluorophenyl)butyl]thio}-1,3,4-oxadiazol-2-yl)benzyl]amino}propyl)phosphonic acid;
(3-{[4-(5-{[1-(3-Nitrophenyl)propyl]thio}-1,3,4-oxadiazol-2-yl)benzyl]amino}propyl)phosphonic acid;
(3-{[4-(5-{[1-(3-nitrophenyl)ethyl]thio}-1,3,4-oxadiazol-2-yl)benzyl]amino}propyl)phosphonic acid;
(3-{[4-(5-{[1-(3-Chloro-2-fluorophenyl)pentyl]thio}-1,3,4-oxadiazol-2-yl)benzyl]amino}propyl)phosphonic acid;
(3-{[4-(5-{[1-(3-Chloro-2-fluorophenyl)hexyl]thio}-1,3,4-oxadiazol-2-yl)benzyl]amino}propyl)phosphonic acid;
(3-{[4-(5-{[1-(3-nitrophenyl)butyl]thio}-1,3,4-oxadiazol-2-yl)benzyl]amino}propyl)phosphonic acid;
(3-{[4-(5-{[1-(3-Bromophenyl)butyl]thio}-1,3,4-oxadiazol-2-yl)benzyl]amino}propyl)phosphonic acid;
(3-((4-(5-((1-(3-Chloro-2-fluorophenyl)heptyl)thio)-1,3,4-oxadiazol-2-yl)benzyl)amino)propyl)phosphonic acid;
3-[(4-{5-[(1-Phenylbutyl)sulfanyl]-1,3,4-oxadiazol-2-yl}benzyl)amino]propanoic acid;
[3-({[4-Methyl-5-(5-{[1-(3-nitrophenyl)ethyl]sulfanyl}-1,3,4-oxadiazol-2-yl)furan-2-yl]methyl}amino)propyl]phosphonic acid;
[3-({[4-Ethyl-5-(5-{[1-(3-nitrophenyl)ethyl]sulfanyl}-1,3,4-oxadiazol-2-yl)furan-2-yl]methyl}amino)propyl]phosphonic acid;
[3-({[4-Ethyl-5-(5-{[1-(3-nitrophenyl)ethyl]sulfanyl}-1,3,4-oxadiazol-2-yl)thiophen-2-yl]methyl}amino)propyl]phosphonic acid; and
[3-({[4-Methyl-5-(5-{[1-(3-nitrophenyl)ethyl]sulfanyl}-1,3,4-oxadiazol-2-yl)thiophen-2-yl]methyl}amino)propyl]phosphonic acid.

6. A pharmaceutical composition comprising as active ingredient a therapeutically effective amount of a compound according to claim 1 and a pharmaceutically acceptable adjuvant, diluent or carrier.

7. A pharmaceutical composition according to claim 6 wherein the compound is selected from:
3-[(4-{5-[(3-Chloro-2-fluorobenzyl)thio]-1,3,4-oxadiazol-2-yl}benzyl)amino]propanoic acid;
2-[(4-{5-[(3-Chloro-2-fluorobenzyl)thio]-1,3,4-oxadiazol-2-yl}benzyl)amino]ethyl dihydrogen phosphate;
2-[(4-{5-[(3-Chloro-2-fluorobenzyl)thio]-1,3,4-oxadiazol-2-yl}benzyl)amino]ethanol;
3-{[3-methyl-4-(5-{[1-(3-nitrophenyl)ethyl]thio}-1,3,4-oxadiazol-2-yl)benzyl]amino}propanoic acid;
(3-{[3-Methyl-4-(5-{[1-(3-nitrophenyl)ethyl]thio}-1,3,4-oxadiazol-2-yl)benzyl]amino}propylphosphonic acid;
(3-{[3-Methyl-4-(5-{[1-(3-nitrophenyl)propyl]thio}-1,3,4-oxadiazol-2-yl)benzyl]amino}propyl)phosphonic acid 3-{[3-Methyl-4-(5-{[1-(3-nitrophenyl)propyl]thio}-1,3,4-oxadiazol-2-yl)benzyl]amino}propanoic acid;
{3-[(4-{5-[(3-Nitrobenzyl)thio]-1,3,4-oxadiazol-2-yl}benzyl)amino]propyl}phosphonic acid;
{3-[(4-{5-[(3,4-Dimethylbenzyl)thio]-1,3,4-oxadiazol-2-yl}benzyl)amino]propyl}phosphonic acid;
(3-{[3-ethyl-4-(5-{[1-(3-Nitrophenyl)ethyl]thio}-1,3,4-oxadiazol-2-yl)benzyl]amino}propyl)phosphonic acid;
(3-{[4-(5-{[1-(3,4-Dimethylphenyl)ethyl]thio}-1,3,4-oxadiazol-2-yl)benzyl]amino}propyl)phosphonic acid;
{3-[(4-{5-[(3-Cyanobenzyl)thio]-1,3,4-oxadiazol-2-yl}benzyl)amino]propyl}phosphonic acid;
{3-[(4-{5-[(1-phenylbutyl)thio]-1,3,4-oxadiazol-2-yl}benzyl)amino]propyl}phosphonic acid;
(3-{[4-(5-{[1-(3-Chloro-2-fluorophenyl)butyl]thio}-1,3,4-oxadiazol-2-yl)benzyl]amino}propyl)phosphonic acid;
(3-{[4-(5-{[1-(3-Nitrophenyl)propyl]thio}-1,3,4-oxadiazol-2-yl)benzyl]amino}propyl)phosphonic acid;
(3-{[4-(5-{[1-(3-nitrophenyl)ethyl]thio}-1,3,4-oxadiazol-2-yl)benzyl]amino}propyl)phosphonic acid;
(3-{[4-(5-{[1-(3-Chloro-2-fluorophenyl)pentyl]thio}-1,3,4-oxadiazol-2-yl)benzyl]amino}propyl)phosphonic acid;
(3-{[4-(5-{[1-(3-Chloro-2-fluorophenyl)hexyl]thio}-1,3,4-oxadiazol-2-yl)benzyl]amino}propyl)phosphonic acid;
(3-{[4-(5-{[1-(3-nitrophenyl)butyl]thio}-1,3,4-oxadiazol-2-yl)benzyl]amino}propyl)phosphonic acid;
(3-{[4-(5-{[1-(3-Bromophenyl)butyl]thio}-1,3,4-oxadiazol-2-yl)benzyl]amino}propyl)phosphonic acid;
(3-((4-(5-((1-(3-Chloro-2-fluorophenyl)heptyl)thio)-1,3,4-oxadiazol-2-yl)benzyl)amino)propyl)phosphonic acid;
3-[(4-{5-[(1-Phenylbutyl)sulfanyl]-1,3,4-oxadiazol-2-yl}benzyl)amino]propanoic acid;
[3-({[4-Methyl-5-(5-{[1-(3-nitrophenyl)ethyl]sulfanyl}-1,3,4-oxadiazol-2-yl)furan-2-yl]methyl}amino)propyl]phosphonic acid;
[3-({[4-Ethyl-5-(5-{[1-(3-nitrophenyl)ethyl]sulfanyl}-1,3,4-oxadiazol-2-yl)furan-2-yl]methyl}amino)propyl]phosphonic acid;
[3-({[4-Ethyl-5-(5-{[1-(3-nitrophenyl)ethyl]sulfanyl}-1,3,4-oxadiazol-2-yl)thiophen-2-yl]methyl}amino)propyl]phosphonic acid; and
[3-({[4-Methyl-5-(5-{[1-(3-nitrophenyl)ethyl]sulfanyl}-1,3,4-oxadiazol-2-yl)thiophen-2-yl]methyl}amino)propyl]phosphonic acid.

8. A method of treating a disorder associated with sphingosine-1-phosphate receptor modulation, which comprises administering to a mammal in need thereof, a pharmaceutical composition comprising a therapeutically effective amount of at least one compound of Formula I
wherein:
X is S, SO or $SO_2$;
$R^1$ is hydrogen, halogen, substituted or unsubstituted $C_{1-8}$ alkyl, $NO_2$, CN, $C(O)R^{13}$ or $OR^{14}$;
$R^2$ is hydrogen, halogen, substituted or unsubstituted $C_{1-8}$ alkyl, $NO_2$, CN, $C(O)R^{13}$ or $OR^{14}$;
$R^3$ is hydrogen, halogen, substituted or unsubstituted $C_{1-8}$ alkyl, $NO_2$, CN, $C(O)R^{13}$ or $OR^{14}$;
$R^4$ is hydrogen, halogen, substituted or unsubstituted $C_{1-8}$ alkyl, $NO_2$, CN, $C(O)R^{13}$ or $OR^{14}$;
$R^5$ is hydrogen, halogen, substituted or unsubstituted $C_{1-8}$ alkyl, $NO_2$, CN, $C(O)R^{13}$ or $OR^{14}$;
$R^6$ is H, halogen, $OR^{14}$, substituted or unsubstituted $C_{1-8}$ alkyl;

$R^7$ is hydrogen, halogen, substituted or unsubstituted $C_{1-8}$ alkyl, $NO_2$, CN, $C(O)R^{13}$ or $OR^{14}$;

$R^8$ is CH, S, O, N, NH or $CH_2$;

$R^9$ is CH or $CH_2$;

$R^{10}$ is hydrogen, halogen, substituted or unsubstituted $C_{1-8}$ alkyl, $C(O)R^{13}$ or $OR^{14}$;

$R^{11}$ is H or substituted or unsubstituted $C_{1-8}$ alkyl;

$R^{12}$ is $OPO_3H_2$, carboxylic acid, $PO_3H_2$, —P(O)MeOH, —P(O)(H)OH or $OR^{14}$;

a is 0 or 1;

b is 1, 2, 3, 4, 5 or 6;

$R^{13}$ is OH or $C_{1-8}$ alkyl;

$R^{14}$ is H or $C_{1-8}$ alkyl;

when a is 1 then

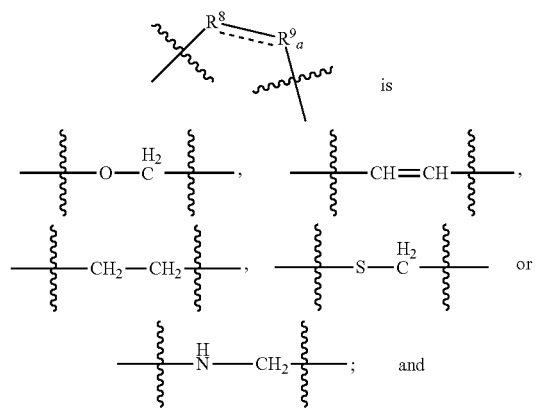

when a is 0 then

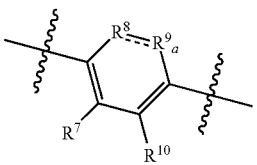 is 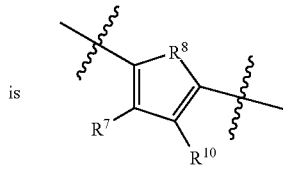

and $R^8$ is S, O, NH or $CH_2$.

9. The method of claim 8, wherein the pharmaceutical composition is administered to the mammal to treat ocular diseases, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, uveitis, scleritis, keratitis, and retinal vasculitis; or systemic vascular barrier related diseases, or autoimmune diseases and immunosuppression, rheumatoid arthritis, Crohn's disease, Graves' disease, inflammatory bowel disease, multiple sclerosis, Myasthenia gravis, Psoriasis, ulcerative colitis, autoimmune uveitis, contact hypersensitivity, atopic dermatitis; or allergies, urticaria, bronchial asthma pulmonary emphysema and chronic obstructive pulmonary diseases.

10. The method of claim 8 wherein the mammal is a human.

* * * * *

UNITED STATES PATENT AND TRADEMARK OFFICE
CERTIFICATE OF CORRECTION

PATENT NO.       : 8,729,110 B1
APPLICATION NO.  : 14/073970
DATED            : May 20, 2014
INVENTOR(S)      : Janet A. Takeuchi et al.

It is certified that error appears in the above-identified patent and that said Letters Patent is hereby corrected as shown below:

In the Specification:

In column 1, line 26, delete "Sphingosine-1 phosphate" and insert -- Sphingosine-1-phosphate --, therefor.

In column 8, line 27, delete ""—C(O)ON"" and insert -- "—C(O)OH". --, therefor.

In column 9, line 56, delete "Stahal" and insert -- Stahl --, therefor.

In column 9, line 65, delete "Stahal" and insert -- Stahl --, therefor.

In column 16, line 3, delete "hydroxide" and insert -- hydroxide. --, therefor.

In column 16, line 19, delete "thriethylamine" and insert -- triethylamine --, therefor.

In column 22, line 4 (Table 2), delete "1 H)," and insert -- 1H), --, therefor.

In column 22, line 5 (Table 2), delete "(S," and insert -- (s, --, therefor.

In column 22, line 27 (Table 2), delete "6H)." and insert -- 6H), --, therefor.

In column 22, line 40 (Table 2), delete "(s." and insert -- (s, --, therefor.

In column 22, line 42 (Table 2), delete "(qj" and insert -- (q j --, therefor.

In column 27, line 24 (Table 4), delete "3 H)." and insert -- 3H). --, therefor.

In columns 35-36, line 48 (Table 5), delete "3 H)," and insert -- 3H), --, therefor.

In columns 37-38, line 6 (Table 5), delete "3 H)," and insert -- 3H), --, therefor.

In columns 45-46, line 24 (Table 6), delete "3 H)," and insert -- 3H), --, therefor.

In columns 47-48, line 5 (Table 7), delete "(d, (d," and insert -- (d, --, therefor.

In columns 57-58, line 33 (Table 7), delete "7.58" and insert -- 7.28 --, therefor.

In column 59, lines 58-59 (Table 7), delete "dithitothreitol" and insert -- dithiothreitol --, therefor.

In column 59, line 63 (Table 7), delete "adenylylimmidodiphosphate" and insert -- adenylylimidodiphosphate --, therefor.

Signed and Sealed this
Fourteenth Day of October, 2014

Michelle K. Lee
*Deputy Director of the United States Patent and Trademark Office*

In the Claims:
In column 62, lines 48-52, in claim 4, delete " 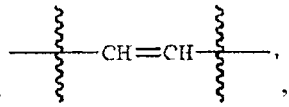 " and insert -- 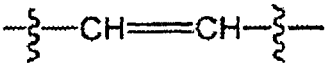 --, therefor.
In column 62, line 67, in claim 4, delete "acid" and insert -- acid; --, therefor.